US008076109B2

(12) United States Patent
Allain et al.

(10) Patent No.: US 8,076,109 B2
(45) Date of Patent: Dec. 13, 2011

(54) PROCESSES FOR PRODUCING A FERMENTATION PRODUCT

(75) Inventors: Eric Allain, Boone, NC (US); Kevin S. Wenger, Wake Forest, NC (US); Henrik Bisgard-Frantzen, Bagsvaerd (DK)

(73) Assignees: Novozymes A/S, Bagsvaerd (DK); Novozymes North America, Inc., Franklinton, NC (US)

( * ) Notice: Subject to any disclaimer, the term of this patent is extended or adjusted under 35 U.S.C. 154(b) by 0 days.

(21) Appl. No.: 13/079,100

(22) Filed: Apr. 4, 2011

(65) Prior Publication Data

US 2011/0183395 A1   Jul. 28, 2011

Related U.S. Application Data

(63) Continuation of application No. 10/586,109, filed as application No. PCT/US2005/001147 on Jan. 14, 2005, now abandoned.

(60) Provisional application No. 60/636,013, filed on Dec. 14, 2004, provisional application No. 60/537,071, filed on Jan. 16, 2004.

(51) Int. Cl.
*C12P 7/00* (2006.01)
*C12P 21/04* (2006.01)
*C12N 9/34* (2006.01)
*C12N 9/28* (2006.01)
*C12N 1/20* (2006.01)
*C12N 15/00* (2006.01)
*C07H 21/04* (2006.01)

(52) U.S. Cl. ..... 435/132; 435/205; 435/202; 435/252.3; 435/320.1; 435/440; 435/69.1; 435/71.1; 536/23.2; 536/23.4

(58) Field of Classification Search .................. None
See application file for complete search history.

(56) References Cited

U.S. PATENT DOCUMENTS

| 4,316,956 A | 2/1982 | Lutzen |
| 4,727,026 A | 2/1988 | Sawada et al. |
| 7,129,069 B2 | 10/2006 | Borchert et al. |
| 7,244,597 B2 | 7/2007 | Veit et al. |
| 7,312,055 B2 | 12/2007 | Borchert et al. |

FOREIGN PATENT DOCUMENTS

| EP | 0140410 B2 | 4/1996 |
| WO | WO 96/23874 | 8/1996 |
| WO | WO 02/38787 A2 | 5/2002 |
| WO | WO 2004/081193 A2 | 9/2004 |
| WO | WO 2004/111218 A2 | 12/2004 |

OTHER PUBLICATIONS

Abe et al., Carbohydrate Research, vol. 175, No. 1, pp. 85-92 (1988).
Hariantono et al., Journal of Fermentation and Bioengineering, vol. 71, No. 5, pp. 367-369 (1991).
Kaneko et al., Journal of Fermentation and Bioengineering, vol. 81, No. 4, pp. 292-298 (1996).
Nagasaka et al., Appl. Microbiol. Biotechnol., vol. 44, pp. 451-458 (1995).
Nagasaka et al., Appl. Microbiol. Biotechnol., vol. 50, pp. 323-330 (1998).

*Primary Examiner* — Yong Pak
(74) *Attorney, Agent, or Firm* — Elias Lambiris

(57) ABSTRACT

The present invention relates to processes for producing a fermentation product, such as ethanol, from milled starch-containing material comprising (a) saccharifying the milled starch-containing material with a glucoamylase having an amino acid sequence shown in SEQ ID NO: 2, or a glucoamylase being at least 70% identical thereto, at a temperature below the initial gelatinization temperature of said starch-containing material, (b) fermenting using a fermenting organism.

20 Claims, No Drawings

SEQUENCE LISTING

```
<160> NUMBER OF SEQ ID NOS: 41

<210> SEQ ID NO 1
<211> LENGTH: 2427
<212> TYPE: DNA
<213> ORGANISM: Athelia rolfsii
<220> FEATURE:
<221> NAME/KEY: sig_peptide
<222> LOCATION: (1)..(54)
<220> FEATURE:
<221> NAME/KEY: CDS
<222> LOCATION: (1)..(208)
<220> FEATURE:
<221> NAME/KEY: mat_peptide
<222> LOCATION: (55)..(2427)
<220> FEATURE:
<221> NAME/KEY: Intron
<222> LOCATION: (209)..(283)
<220> FEATURE:
<221> NAME/KEY: CDS
<222> LOCATION: (284)..(354)
<220> FEATURE:
<221> NAME/KEY: Intron
<222> LOCATION: (355)..(410)
<220> FEATURE:
<221> NAME/KEY: misc_feature
<222> LOCATION: (367)..(367)
<223> OTHER INFORMATION: n is a, c, g or t.
<220> FEATURE:
<221> NAME/KEY: misc_feature
<222> LOCATION: (392)..(392)
<223> OTHER INFORMATION: n is a, c, g or t
<220> FEATURE:
<221> NAME/KEY: CDS
<222> LOCATION: (411)..(557)
<220> FEATURE:
<221> NAME/KEY: Intron
<222> LOCATION: (558)..(616)
<220> FEATURE:
<221> NAME/KEY: CDS
<222> LOCATION: (617)..(770)
<220> FEATURE:
<221> NAME/KEY: Intron
<222> LOCATION: (771)..(825)
<220> FEATURE:
<221> NAME/KEY: CDS
<222> LOCATION: (826)..(986)
<220> FEATURE:
<221> NAME/KEY: Intron
<222> LOCATION: (987)..(1058)
<220> FEATURE:
<221> NAME/KEY: CDS
<222> LOCATION: (1059)..(1331)
<220> FEATURE:
<221> NAME/KEY: Intron
<222> LOCATION: (1332)..(1409)
<220> FEATURE:
<221> NAME/KEY: CDS
<222> LOCATION: (1410)..(1713)
<220> FEATURE:
<221> NAME/KEY: Intron
<222> LOCATION: (1714)..(1787)
<220> FEATURE:
<221> NAME/KEY: CDS
```

```
<222> LOCATION: (1788)..(1958)
<220> FEATURE:
<221> NAME/KEY: Intron
<222> LOCATION: (1959)..(2020)
<220> FEATURE:
<221> NAME/KEY: CDS
<222> LOCATION: (2021)..(2116)
<220> FEATURE:
<221> NAME/KEY: Intron
<222> LOCATION: (2117)..(2173)
<220> FEATURE:
<221> NAME/KEY: CDS
<222> LOCATION: (2174)..(2325)

<400> SEQUENCE: 1
```

| | | | | | | | | | | | | | | | | |
|---|---|---|---|---|---|---|---|---|---|---|---|---|---|---|---|---|
| atg | ttt | cgt | tca | ctc | ctg | gcc | ttg | gct | gcg | tgt | gca | gtc | gcc | tct | gta | 48 |
| Met | Phe | Arg | Ser | Leu | Leu | Ala | Leu | Ala | Ala | Cys | Ala | Val | Ala | Ser | Val | |
| | | | -15 | | | | -10 | | | | -5 | | | | | |

| | | | | | | | | | | | | | | | | |
|---|---|---|---|---|---|---|---|---|---|---|---|---|---|---|---|---|
| tct | gca | cag | tct | gcg | tct | gcg | aca | gca | tat | ctt | acc | aag | gaa | tct | gca | 96 |
| Ser | Ala | Gln | Ser | Ala | Ser | Ala | Thr | Ala | Tyr | Leu | Thr | Lys | Glu | Ser | Ala | |
| | | -1 | 1 | | | | 5 | | | | | 10 | | | | |

| | | | | | | | | | | | | | | | | |
|---|---|---|---|---|---|---|---|---|---|---|---|---|---|---|---|---|
| gtt | gcc | aag | aat | ggc | gta | ctt | tgc | aac | att | ggt | agc | cag | gga | tgc | atg | 144 |
| Val | Ala | Lys | Asn | Gly | Val | Leu | Cys | Asn | Ile | Gly | Ser | Gln | Gly | Cys | Met | |
| 15 | | | | 20 | | | | | 25 | | | | | 30 | | |

| | | | | | | | | | | | | | | | | |
|---|---|---|---|---|---|---|---|---|---|---|---|---|---|---|---|---|
| tct | gag | ggt | gcc | tat | agc | ggt | att | gtg | atc | gca | tct | ccc | tct | aaa | act | 192 |
| Ser | Glu | Gly | Ala | Tyr | Ser | Gly | Ile | Val | Ile | Ala | Ser | Pro | Ser | Lys | Thr | |
| | | | | 35 | | | | | 40 | | | | 45 | | | |

| | | | | |
|---|---|---|---|---|
| agc cct gac tat ctc t gtgagtatta tttgtaaagt agcctcactg atagtacatt | 248 |
| Ser Pro Asp Tyr Leu | |
| 50 | |

| | | |
|---|---|---|
| ttctgagttc tgttacaacc ctggtattat aatag at  acc tgg act cgc gac | 300 |
| Tyr Thr Trp Thr Arg Asp | |
| 55 | |

| | | | | | | | | | | | | | | |
|---|---|---|---|---|---|---|---|---|---|---|---|---|---|---|
| tcg | tcg | ctc | gtc | ttc | aag | atg | tta | att | gac | caa | tac | aca | aat | ggc | ctg | 348 |
| Ser | Ser | Leu | Val | Phe | Lys | Met | Leu | Ile | Asp | Gln | Tyr | Thr | Asn | Gly | Leu |
| | | 60 | | | | | 65 | | | | | 70 | | | |

| | | |
|---|---|---|
| gat acg gtatgtggca tcngcgttcc ggctcgcctc aaagatgnaa aattgatgtt | 404 |
| Asp Thr | |
| 75 | |

| | | | | | | | | | | | | | | |
|---|---|---|---|---|---|---|---|---|---|---|---|---|---|---|
| tcttag | aca | ctg | cgc | act | ctc | att | gac | gag | ttt | gtc | tct | gcg | gaa | gcc | 452 |
| | Thr | Leu | Arg | Thr | Leu | Ile | Asp | Glu | Phe | Val | Ser | Ala | Glu | Ala | |
| | | | | 80 | | | | | 85 | | | | | | |

| | | | | | | | | | | | | | | | |
|---|---|---|---|---|---|---|---|---|---|---|---|---|---|---|---|
| acc | att | caa | caa | acc | agt | aac | cca | tct | ggt | acc | gtc | tct | acc | ggt | ggt | 500 |
| Thr | Ile | Gln | Gln | Thr | Ser | Asn | Pro | Ser | Gly | Thr | Val | Ser | Thr | Gly | Gly |
| 90 | | | | | 95 | | | | | 100 | | | | | 105 |

| | | | | | | | | | | | | | | | |
|---|---|---|---|---|---|---|---|---|---|---|---|---|---|---|---|
| ctc | ggc | gaa | ccc | aaa | ttc | aat | atc | gac | gag | acg | gca | ttt | acg | ggc | gca | 548 |
| Leu | Gly | Glu | Pro | Lys | Phe | Asn | Ile | Asp | Glu | Thr | Ala | Phe | Thr | Gly | Ala |
| | | | | 110 | | | | | 115 | | | | | 120 | |

| | |
|---|---|
| tgg ggt cgt gtaagctacc aatacacaat caaaatcgac catctgtatt | 597 |
| Trp Gly Arg | |

| | | | | | | | | | | |
|---|---|---|---|---|---|---|---|---|---|---|
| tactatctat aatttctag ccc | caa | cgt | gat | ggt | ccc | gcc | ctc | cgt | gca | acc | 649 |
| | Pro | Gln | Arg | Asp | Gly | Pro | Ala | Leu | Arg | Ala | Thr |
| | | 125 | | | | 130 | | | | 135 | |

| | | | | | | | | | | | | | | | |
|---|---|---|---|---|---|---|---|---|---|---|---|---|---|---|---|
| gca | atc | atg | acc | tat | gcg | acg | tat | ctg | tac | aac | aat | ggc | aac | act | tcc | 697 |
| Ala | Ile | Met | Thr | Tyr | Ala | Thr | Tyr | Leu | Tyr | Asn | Asn | Gly | Asn | Thr | Ser |
| | | | 140 | | | | | 145 | | | | | 150 | | |

| | | | | | | | | | | | | | | | |
|---|---|---|---|---|---|---|---|---|---|---|---|---|---|---|---|
| tac | gtg | acc | aac | acc | ctt | tgg | cct | atc | atc | aag | ctc | gac | ctt | gac | tat | 745 |
| Tyr | Val | Thr | Asn | Thr | Leu | Trp | Pro | Ile | Ile | Lys | Leu | Asp | Leu | Asp | Tyr |
| | | 155 | | | | | 160 | | | | | 165 | | | |

| | | | | | | | |
|---|---|---|---|---|---|---|---|
| gtc | aac | tcg | gac | tgg | aac | cag | acc a gtaagcgaat ttctaggggg | 790 |
| Val | Asn | Ser | Asp | Trp | Asn | Gln | Thr |
| | 170 | | | | | 175 | |

| | |
|---|---|
| acttatctaa aacagcatat tcaaccagta aatag cg  ttt gac ctc tgg gaa | 842 |

```
                    Thr Phe Asp Leu Trp Glu
                                        180 gaa gtt gac tcg tct tct ttc ttt acg act gcc gtt cag cac cgt gct        890
Glu Val Asp Ser Ser Ser Phe Phe Thr Thr Ala Val Gln His Arg Ala
            185                 190                 195 ctt gtt cag ggc gca gcc ttt gct acc ctc atc ggc caa act tcg tct        938
Leu Val Gln Gly Ala Ala Phe Ala Thr Leu Ile Gly Gln Thr Ser Ser
            200                 205                 210 gct tcg act tac tcc gcc acg gcc cct agc att ctc tgc ttc ttg cag        986
Ala Ser Thr Tyr Ser Ala Thr Ala Pro Ser Ile Leu Cys Phe Leu Gln
            215                 220                 225 gtgagataaa aatctttcta tgtaattggt ttttcccctc aaattgaaat tgacatattt     1046
gcgatccaat ag tct tac tgg aac acc aac gga tac tgg acg gcc aac act    1097
              Ser Tyr Trp Asn Thr Asn Gly Tyr Trp Thr Ala Asn Thr
              230                 235                 240 ggt ggc gga cgt tcc ggc aag gac gcc aac acc ata ctc gct tct atc       1145
Gly Gly Gly Arg Ser Gly Lys Asp Ala Asn Thr Ile Leu Ala Ser Ile
            245                 250                 255 cac aca ttt gac gcc agc gcc ggc tgc tct gct gcc acg tct caa cca       1193
His Thr Phe Asp Ala Ser Ala Gly Cys Ser Ala Ala Thr Ser Gln Pro
            260                 265                 270 tgc tct gac gta gca ttg gcc aac ctg aag gta tac gtt gac tct ttc       1241
Cys Ser Asp Val Ala Leu Ala Asn Leu Lys Val Tyr Val Asp Ser Phe
275                 280                 285                 290 cgt agt att tat acg atc aac agc ggt att tcc tct acc tcg ggt gtt       1289
Arg Ser Ile Tyr Thr Ile Asn Ser Gly Ile Ser Ser Thr Ser Gly Val
                295                 300                 305 gct act ggt cgc tac ccc gaa gat tcg tat tac aat ggc aac               1331
Ala Thr Gly Arg Tyr Pro Glu Asp Ser Tyr Tyr Asn Gly Asn
            310                 315                 320 gtacgtattt atctaatttt tccaagacag tcaaagttta tgttcatctg cccccttta      1391 cctgtacatt caaaatag ccc tgg tac ctc tgc aca ctc gcc gtc gcc gag      1442
                    Pro Trp Tyr Leu Cys Thr Leu Ala Val Ala Glu
                                    325                 330 cag ctc tat gat gct ctc atc gta tgg aag gct gcc ggg gag ctc aac       1490
Gln Leu Tyr Asp Ala Leu Ile Val Trp Lys Ala Ala Gly Glu Leu Asn
            335                 340                 345 gtc acc tcc gtc tcg ctc gcg ttc ttc cag caa ttc gac tcg agc atc       1538
Val Thr Ser Val Ser Leu Ala Phe Phe Gln Gln Phe Asp Ser Ser Ile
            350                 355                 360 acc gcc ggc act tac gcc tcc tcg tcg agc gta tac act tcg ctc atc       1586
Thr Ala Gly Thr Tyr Ala Ser Ser Ser Ser Val Tyr Thr Ser Leu Ile
            365                 370                 375 tct gac atc cag gcg ttc gca gac gag ttt gtt gac att gtt gcc aag       1634
Ser Asp Ile Gln Ala Phe Ala Asp Glu Phe Val Asp Ile Val Ala Lys
380                 385                 390                 395 tac acg cct tcg tct ggc ttc ttg tct gag cag tat gat aag tcc acg       1682
Tyr Thr Pro Ser Ser Gly Phe Leu Ser Glu Gln Tyr Asp Lys Ser Thr
                400                 405                 410 ggt gct cag gat tcg gct gct aac ttg act t gtaagtcatc tatttgttca      1733
Gly Ala Gln Asp Ser Ala Ala Asn Leu Thr
            415                 420 ttctattcct tttcaaaaaa aaaagtgatg ctaatgattt ttggcggaaa ccag gg        1789
                                                             Trp tcc tat gct gct gct atc acc gct tac caa gcc cgc aat ggc ttc aca       1837
Ser Tyr Ala Ala Ala Ile Thr Ala Tyr Gln Ala Arg Asn Gly Phe Thr
            425                 430                 435 ggt gct tcg tgg ggt gct aag gga gtt tct acc tcc tgc tcg act ggt       1885
Gly Ala Ser Trp Gly Ala Lys Gly Val Ser Thr Ser Cys Ser Thr Gly
```

-continued

```
                    440                 445                 450
gct aca agc ccg ggt ggc tcc tcg ggt agt gtc gag gtc act ttc gac    1933
Ala Thr Ser Pro Gly Gly Ser Ser Gly Ser Val Glu Val Thr Phe Asp
455                 460                 465                 470 gtt tac gct acc aca gta tat ggc c gtaagcactt gactagcttc            1978
Val Tyr Ala Thr Thr Val Tyr Gly
                475 aaaccatact tcatcatgct gataaacaaa aaatgaaac ag ag  aac atc tat      2031
                                              Gln Asn Ile Tyr
                                                      480 atc acc ggt gat gtg agt gag ctc ggc aac tgg aca ccc gcc aat ggt    2079
Ile Thr Gly Asp Val Ser Glu Leu Gly Asn Trp Thr Pro Ala Asn Gly
                485                 490                 495 gtt gca ctc tct tct gct aac tac ccc acc tgg agt g gtaagttgac       2126
Val Ala Leu Ser Ser Ala Asn Tyr Pro Thr Trp Ser
500                 505                 510 ccttaccagt atcttgacag acattgatat tgacttccgc aatacag cc  acg atc    2181
                                                       Ala Thr Ile gct ctc ccc gct gac acg aca atc cag tac aag tat gtc aac att gac    2229
Ala Leu Pro Ala Asp Thr Thr Ile Gln Tyr Lys Tyr Val Asn Ile Asp
515                 520                 525 ggc agc acc gtc atc tgg gag gat gct atc agc aat cgc gag atc acg    2277
Gly Ser Thr Val Ile Trp Glu Asp Ala Ile Ser Asn Arg Glu Ile Thr
530                 535                 540                 545 acg ccc gcc agc ggc aca tac acc gaa aaa gac act tgg gat gaa tct    2325
Thr Pro Ala Ser Gly Thr Tyr Thr Glu Lys Asp Thr Trp Asp Glu Ser
                550                 555                 560 taaactgctg aacttgaacg gcttgcaaaa gcgaatggtg tagaaaataa acgaagattt  2385
tgattgcttt gttttgtttc tcttcctatc ttgtttctct ag                    2427
```

<210> SEQ ID NO 2
<211> LENGTH: 579
<212> TYPE: PRT
<213> ORGANISM: Athelia rolfsii

<400> SEQUENCE: 2

```
Met Phe Arg Ser Leu Leu Ala Leu Ala Ala Cys Ala Val Ala Ser Val
                -15                 -10                 -5

Ser Ala Gln Ser Ala Ser Ala Thr Ala Tyr Leu Thr Lys Glu Ser Ala
     -1  1                   5                  10

Val Ala Lys Asn Gly Val Leu Cys Asn Ile Gly Ser Gln Gly Cys Met
15                  20                  25                  30

Ser Glu Gly Ala Tyr Ser Gly Ile Val Ile Ala Ser Pro Ser Lys Thr
                35                  40                  45

Ser Pro Asp Tyr Leu Tyr Thr Trp Thr Arg Asp Ser Ser Leu Val Phe
                50                  55                  60

Lys Met Leu Ile Asp Gln Tyr Thr Asn Gly Leu Asp Thr Thr Leu Arg
            65                  70                  75

Thr Leu Ile Asp Glu Phe Val Ser Ala Glu Ala Thr Ile Gln Gln Thr
        80                  85                  90

Ser Asn Pro Ser Gly Thr Val Ser Thr Gly Gly Leu Gly Glu Pro Lys
95                  100                 105                 110

Phe Asn Ile Asp Glu Thr Ala Phe Thr Gly Ala Trp Gly Arg Pro Gln
                115                 120                 125

Arg Asp Gly Pro Ala Leu Arg Ala Thr Ala Ile Met Thr Tyr Ala Thr
            130                 135                 140

Tyr Leu Tyr Asn Asn Gly Asn Thr Ser Tyr Val Thr Asn Thr Leu Trp
```

```
                145                 150                 155
Pro Ile Ile Lys Leu Asp Leu Asp Tyr Val Asn Ser Asp Trp Asn Gln
160                 165                 170

Thr Thr Phe Asp Leu Trp Glu Glu Val Asp Ser Ser Phe Phe Thr
175                 180                 185                 190

Thr Ala Val Gln His Arg Ala Leu Val Gln Gly Ala Ala Phe Ala Thr
            195                 200                 205

Leu Ile Gly Gln Thr Ser Ser Ala Ser Thr Tyr Ser Ala Thr Ala Pro
            210                 215                 220

Ser Ile Leu Cys Phe Leu Gln Ser Tyr Trp Asn Thr Asn Gly Tyr Trp
            225                 230                 235

Thr Ala Asn Thr Gly Gly Arg Ser Gly Lys Asp Ala Asn Thr Ile
240                 245                 250

Leu Ala Ser Ile His Thr Phe Asp Ala Ser Ala Gly Cys Ser Ala Ala
255                 260                 265                 270

Thr Ser Gln Pro Cys Ser Asp Val Ala Leu Ala Asn Leu Lys Val Tyr
                275                 280                 285

Val Asp Ser Phe Arg Ser Ile Tyr Thr Ile Asn Ser Gly Ile Ser Ser
            290                 295                 300

Thr Ser Gly Val Ala Thr Gly Arg Tyr Pro Glu Asp Ser Tyr Tyr Asn
            305                 310                 315

Gly Asn Pro Trp Tyr Leu Cys Thr Leu Ala Val Ala Glu Gln Leu Tyr
320                 325                 330

Asp Ala Leu Ile Val Trp Lys Ala Ala Gly Glu Leu Asn Val Thr Ser
335                 340                 345                 350

Val Ser Leu Ala Phe Phe Gln Gln Phe Asp Ser Ser Ile Thr Ala Gly
                355                 360                 365

Thr Tyr Ala Ser Ser Ser Ser Val Tyr Thr Ser Leu Ile Ser Asp Ile
            370                 375                 380

Gln Ala Phe Ala Asp Glu Phe Val Asp Ile Val Ala Lys Tyr Thr Pro
            385                 390                 395

Ser Ser Gly Phe Leu Ser Glu Gln Tyr Asp Lys Ser Thr Gly Ala Gln
400                 405                 410

Asp Ser Ala Ala Asn Leu Thr Trp Ser Tyr Ala Ala Ile Thr Ala
415                 420                 425                 430

Tyr Gln Ala Arg Asn Gly Phe Thr Gly Ala Ser Trp Gly Ala Lys Gly
                435                 440                 445

Val Ser Thr Ser Cys Ser Thr Gly Ala Thr Ser Pro Gly Gly Ser Ser
            450                 455                 460

Gly Ser Val Glu Val Thr Phe Asp Val Tyr Ala Thr Thr Val Tyr Gly
            465                 470                 475

Gln Asn Ile Tyr Ile Thr Gly Asp Val Ser Glu Leu Gly Asn Trp Thr
            480                 485                 490

Pro Ala Asn Gly Val Ala Leu Ser Ala Asn Tyr Pro Thr Trp Ser
495                 500                 505                 510

Ala Thr Ile Ala Leu Pro Ala Asp Thr Thr Ile Gln Tyr Lys Tyr Val
                515                 520                 525

Asn Ile Asp Gly Ser Thr Val Ile Trp Glu Asp Ala Ile Ser Asn Arg
            530                 535                 540

Glu Ile Thr Thr Pro Ala Ser Gly Thr Tyr Thr Glu Lys Asp Thr Trp
            545                 550                 555

Asp Glu Ser
560
```

```
<210> SEQ ID NO 3
<211> LENGTH: 484
<212> TYPE: PRT
<213> ORGANISM: Aspergillus niger
<220> FEATURE:
<221> NAME/KEY: mat_peptide
<222> LOCATION: (1)..(484)

<400> SEQUENCE: 3
```

| | | | | | | | | | | | | | | | |
|---|---|---|---|---|---|---|---|---|---|---|---|---|---|---|---|
| Leu | Ser | Ala | Ala | Ser | Trp | Arg | Thr | Gln | Ser | Ile | Tyr | Phe | Leu | Leu | Thr |
| 1 | | | | 5 | | | | | 10 | | | | | 15 | |
| Asp | Arg | Phe | Gly | Arg | Thr | Asp | Asn | Ser | Thr | Thr | Ala | Thr | Cys | Asn | Thr |
| | | | 20 | | | | | 25 | | | | | 30 | | |
| Gly | Asn | Glu | Ile | Tyr | Cys | Gly | Gly | Ser | Trp | Gln | Gly | Ile | Ile | Asp | His |
| | | 35 | | | | | 40 | | | | | 45 | | | |
| Leu | Asp | Tyr | Ile | Glu | Gly | Met | Gly | Phe | Thr | Ala | Ile | Trp | Ile | Ser | Pro |
| | 50 | | | | | 55 | | | | | 60 | | | | |
| Ile | Thr | Glu | Gln | Leu | Pro | Gln | Asp | Thr | Ala | Asp | Gly | Glu | Ala | Tyr | His |
| 65 | | | | | 70 | | | | | 75 | | | | | 80 |
| Gly | Tyr | Trp | Gln | Gln | Lys | Ile | Tyr | Asp | Val | Asn | Ser | Asn | Phe | Gly | Thr |
| | | | | 85 | | | | | 90 | | | | | 95 | |
| Ala | Asp | Asn | Leu | Lys | Ser | Leu | Ser | Asp | Ala | Leu | His | Ala | Arg | Gly | Met |
| | | | 100 | | | | | 105 | | | | | 110 | | |
| Tyr | Leu | Met | Val | Asp | Val | Val | Pro | Asp | His | Met | Gly | Tyr | Ala | Gly | Asn |
| | | 115 | | | | | 120 | | | | | 125 | | | |
| Gly | Asn | Asp | Val | Asp | Tyr | Ser | Val | Phe | Asp | Pro | Phe | Asp | Ser | Ser | Ser |
| | 130 | | | | | 135 | | | | | 140 | | | | |
| Tyr | Phe | His | Pro | Tyr | Cys | Leu | Ile | Thr | Asp | Trp | Asp | Asn | Leu | Thr | Met |
| 145 | | | | | 150 | | | | | 155 | | | | | 160 |
| Val | Glu | Asp | Cys | Trp | Glu | Gly | Asp | Thr | Ile | Val | Ser | Leu | Pro | Asp | Leu |
| | | | | 165 | | | | | 170 | | | | | 175 | |
| Asp | Thr | Thr | Glu | Thr | Ala | Val | Arg | Thr | Ile | Trp | Tyr | Asp | Trp | Val | Ala |
| | | | 180 | | | | | 185 | | | | | 190 | | |
| Asp | Leu | Val | Ser | Asn | Tyr | Ser | Val | Asp | Gly | Leu | Arg | Ile | Asp | Ser | Val |
| | | 195 | | | | | 200 | | | | | 205 | | | |
| Leu | Glu | Val | Gln | Pro | Asp | Phe | Phe | Pro | Gly | Tyr | Asn | Lys | Ala | Ser | Gly |
| | 210 | | | | | 215 | | | | | 220 | | | | |
| Val | Tyr | Cys | Val | Gly | Glu | Ile | Asp | Asn | Gly | Asn | Pro | Ala | Ser | Asp | Cys |
| 225 | | | | | 230 | | | | | 235 | | | | | 240 |
| Pro | Tyr | Gln | Lys | Val | Leu | Asp | Gly | Val | Leu | Asn | Tyr | Pro | Ile | Tyr | Trp |
| | | | | 245 | | | | | 250 | | | | | 255 | |
| Gln | Leu | Leu | Tyr | Ala | Phe | Glu | Ser | Ser | Gly | Ser | Ile | Ser | Asn | Leu |
| | | | 260 | | | | | 265 | | | | | 270 | | |
| Tyr | Asn | Met | Ile | Lys | Ser | Val | Ala | Ser | Asp | Cys | Ser | Asp | Pro | Thr | Leu |
| | | 275 | | | | | 280 | | | | | 285 | | | |
| Leu | Gly | Asn | Phe | Ile | Glu | Asn | His | Asp | Asn | Pro | Arg | Phe | Ala | Lys | Tyr |
| | 290 | | | | | 295 | | | | | 300 | | | | |
| Thr | Ser | Asp | Tyr | Ser | Gln | Ala | Lys | Asn | Val | Leu | Ser | Tyr | Ile | Phe | Leu |
| 305 | | | | | 310 | | | | | 315 | | | | | 320 |
| Ser | Asp | Gly | Ile | Pro | Ile | Val | Tyr | Ala | Gly | Glu | Glu | Gln | His | Tyr | Ala |
| | | | | 325 | | | | | 330 | | | | | 335 | |
| Gly | Gly | Lys | Val | Pro | Tyr | Asn | Arg | Glu | Ala | Thr | Trp | Leu | Ser | Gly | Tyr |
| | | | 340 | | | | | 345 | | | | | 350 | | |
| Asp | Thr | Ser | Ala | Glu | Leu | Tyr | Thr | Trp | Ile | Ala | Thr | Thr | Asn | Ala | Ile |
| | | 355 | | | | | 360 | | | | | 365 | | | |

```
Arg Lys Leu Ala Ile Ala Ala Asp Ser Ala Tyr Ile Thr Tyr Ala Asn
        370                 375                 380

Asp Ala Phe Tyr Thr Asp Ser Asn Thr Ile Ala Met Ala Lys Gly Thr
385                 390                 395                 400

Ser Gly Ser Gln Val Ile Thr Val Leu Ser Asn Lys Gly Ser Ser Gly
                    405                 410                 415

Ser Ser Tyr Thr Leu Thr Leu Ser Gly Ser Gly Tyr Thr Ser Gly Thr
                420                 425                 430

Lys Leu Ile Glu Ala Tyr Thr Cys Thr Ser Val Thr Val Asp Ser Ser
            435                 440                 445

Gly Asp Ile Pro Val Pro Met Ala Ser Gly Leu Pro Arg Val Leu Leu
450                 455                 460

Pro Ala Ser Val Val Asp Ser Ser Ser Leu Cys Gly Gly Ser Gly Arg
465                 470                 475                 480

Leu Tyr Val Glu

<210> SEQ ID NO 4
<211> LENGTH: 498
<212> TYPE: PRT
<213> ORGANISM: Aspergillus oryzae
<220> FEATURE:
<221> NAME/KEY: SIGNAL
<222> LOCATION: (1)..(19)
<220> FEATURE:
<221> NAME/KEY: mat_peptide
<222> LOCATION: (20)..(498)

<400> SEQUENCE: 4

Met Val Ala Trp Trp Ser Leu Phe Leu Tyr Gly Leu Gln Val Ala Ala
                -15                 -10                 -5

Pro Ala Leu Ala Ala Thr Pro Ala Asp Trp Arg Ser Gln Ser Ile Tyr
            -1   1               5                  10

Phe Leu Leu Thr Asp Arg Phe Ala Arg Thr Asp Gly Ser Thr Thr Ala
        15                  20                  25

Thr Cys Asn Thr Ala Asp Gln Lys Tyr Cys Gly Gly Thr Trp Gln Gly
30                  35                  40                  45

Ile Ile Asp Lys Leu Asp Tyr Ile Gln Gly Met Gly Phe Thr Ala Ile
                50                  55                  60

Trp Ile Thr Pro Val Thr Ala Gln Leu Pro Gln Thr Thr Ala Tyr Gly
            65                  70                  75

Asp Ala Tyr His Gly Tyr Trp Gln Gln Asp Ile Tyr Ser Leu Asn Glu
        80                  85                  90

Asn Tyr Gly Thr Ala Asp Asp Leu Lys Ala Leu Ser Ser Ala Leu His
95                  100                 105

Glu Arg Gly Met Tyr Leu Met Val Asp Val Val Ala Asn His Met Gly
110                 115                 120                 125

Tyr Asp Gly Ala Gly Ser Ser Val Asp Tyr Ser Val Phe Lys Pro Phe
                130                 135                 140

Ser Ser Gln Asp Tyr Phe His Pro Phe Cys Phe Ile Gln Asn Tyr Glu
            145                 150                 155

Asp Gln Thr Gln Val Glu Asp Cys Trp Leu Gly Asp Asn Thr Val Ser
        160                 165                 170

Leu Pro Asp Leu Asp Thr Thr Lys Asp Val Val Lys Asn Glu Trp Tyr
    175                 180                 185

Asp Trp Val Gly Ser Leu Val Ser Asn Tyr Ser Ile Asp Gly Leu Arg
190                 195                 200                 205

Ile Asp Thr Val Lys His Val Gln Lys Asp Phe Trp Pro Gly Tyr Asn
```

```
                       210                 215                 220
Lys Ala Ala Gly Val Tyr Cys Ile Gly Glu Val Leu Asp Gly Asp Pro
                225                 230                 235

Ala Tyr Thr Cys Pro Tyr Gln Asn Val Met Asp Gly Val Leu Asn Tyr
            240                 245                 250

Pro Ile Tyr Tyr Pro Leu Leu Asn Ala Phe Lys Ser Thr Ser Gly Ser
        255                 260                 265

Met Asp Asp Leu Tyr Asn Met Ile Asn Thr Val Lys Ser Asp Cys Pro
270                 275                 280                 285

Asp Ser Thr Leu Leu Gly Thr Phe Val Glu Asn His Asp Asn Pro Arg
                290                 295                 300

Phe Ala Ser Tyr Thr Asn Asp Ile Ala Leu Ala Lys Asn Val Ala Ala
            305                 310                 315

Phe Ile Ile Leu Asn Asp Gly Ile Pro Ile Ile Tyr Ala Gly Gln Glu
        320                 325                 330

Gln His Tyr Ala Gly Gly Asn Asp Pro Ala Asn Arg Glu Ala Thr Trp
    335                 340                 345

Leu Ser Gly Tyr Pro Thr Asp Ser Glu Leu Tyr Lys Leu Ile Ala Ser
350                 355                 360                 365

Ala Asn Ala Ile Arg Asn Tyr Ala Ile Ser Lys Asp Thr Gly Phe Val
                370                 375                 380

Thr Tyr Lys Asn Trp Pro Ile Tyr Lys Asp Asp Thr Thr Ile Ala Met
            385                 390                 395

Arg Lys Gly Thr Asp Gly Ser Gln Ile Val Thr Ile Leu Ser Asn Lys
        400                 405                 410

Gly Ala Ser Gly Asp Ser Tyr Thr Leu Ser Leu Ser Gly Ala Gly Tyr
    415                 420                 425

Thr Ala Gly Gln Gln Leu Thr Glu Val Ile Gly Cys Thr Thr Val Thr
430                 435                 440                 445

Val Gly Ser Asp Gly Asn Val Pro Val Pro Met Ala Gly Gly Leu Pro
                450                 455                 460

Arg Val Leu Tyr Pro Thr Glu Lys Leu Ala Gly Ser Lys Ile Cys Ser
            465                 470                 475

Ser Ser

<210> SEQ ID NO 5
<211> LENGTH: 483
<212> TYPE: PRT
<213> ORGANISM: Bacillus licheniformis
<220> FEATURE:
<221> NAME/KEY: mat_peptide
<222> LOCATION: (1)..(483)

<400> SEQUENCE: 5

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
                20                  25                  30

Ala Glu His Gly Ile Thr Ala Val Trp Ile Pro Pro Ala Tyr Lys Gly
            35                  40                  45

Thr Ser Gln Ala Asp Val Gly Tyr Gly Ala Tyr Asp Leu Tyr Asp Leu
        50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95
```

```
Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 6
<211> LENGTH: 480
<212> TYPE: PRT
<213> ORGANISM: Bacillus amyloliquefaciens
```

-continued

```
<220> FEATURE:
<221> NAME/KEY: mat_peptide
<222> LOCATION: (1)..(480)

<400> SEQUENCE: 6

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400
```

```
Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

<210> SEQ ID NO 7
<211> LENGTH: 514
<212> TYPE: PRT
<213> ORGANISM: Bacillus stearothermophilus
<220> FEATURE:
<221> NAME/KEY: mat_peptide
<222> LOCATION: (1)..(514)

<400> SEQUENCE: 7

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Ser Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
        275                 280                 285
```

```
Ala Pro Leu His Asn Lys Phe Tyr Thr Ala Ser Lys Ser Gly Gly Thr
        290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
            325                 330                 335

Ala Leu Gln Ser Trp Val Asp Pro Trp Phe Lys Pro Leu Ala Tyr Ala
        340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
            405                 410                 415

Thr Glu Lys Pro Gly Ser Gly Leu Ala Ala Leu Ile Thr Asp Gly Pro
        420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Ser Ile Thr Thr
            485                 490                 495

Arg Pro Trp Thr Asp Glu Phe Val Arg Trp Thr Glu Pro Arg Leu Val
            500                 505                 510

Ala Trp

<210> SEQ ID NO 8
<211> LENGTH: 38
<212> TYPE: PRT
<213> ORGANISM: Aspergillus niger
<220> FEATURE:
<221> NAME/KEY: MISC_FEATURE
<222> LOCATION: (1)..(38)
<223> OTHER INFORMATION: linker sequence

<400> SEQUENCE: 8

Thr Gly Gly Thr Thr Thr Thr Ala Thr Pro Thr Gly Ser Gly Ser Val
1               5                   10                  15

Thr Ser Thr Ser Lys Thr Thr Ala Thr Ala Ser Lys Thr Ser Thr Ser
            20                  25                  30

Thr Ser Ser Thr Ser Ala
        35

<210> SEQ ID NO 9
<211> LENGTH: 31
<212> TYPE: PRT
<213> ORGANISM: Aspergillus kawachi
<220> FEATURE:
<221> NAME/KEY: MISC_FEATURE
<222> LOCATION: (1)..(31)
<223> OTHER INFORMATION: linker sequence

<400> SEQUENCE: 9

Thr Thr Thr Thr Thr Thr Ala Ala Ala Thr Ser Thr Ser Lys Ala Thr
1               5                   10                  15
```

```
Thr Ser Ser Ser Ser Ser Ser Ala Ala Ala Thr Thr Ser Ser Ser
            20                  25                  30
```

<210> SEQ ID NO 10
<211> LENGTH: 11
<212> TYPE: PRT
<213> ORGANISM: Athelia rolfsii
<220> FEATURE:
<221> NAME/KEY: MISC_FEATURE
<222> LOCATION: (1)..(11)
<223> OTHER INFORMATION: linker sequence

<400> SEQUENCE: 10

```
Gly Ala Thr Ser Pro Gly Gly Ser Ser Gly Ser
1               5                   10
```

<210> SEQ ID NO 11
<211> LENGTH: 8
<212> TYPE: PRT
<213> ORGANISM: Artificial sequence
<220> FEATURE:
<223> OTHER INFORMATION: PEPT linker
<220> FEATURE:
<221> NAME/KEY: MISC_FEATURE
<222> LOCATION: (1)..(8)
<223> OTHER INFORMATION: linker sequence

<400> SEQUENCE: 11

```
Pro Glu Pro Thr Pro Glu Pro Thr
1               5
```

<210> SEQ ID NO 12
<211> LENGTH: 396
<212> TYPE: DNA
<213> ORGANISM: Aspergillus kawachi
<220> FEATURE:
<221> NAME/KEY: CDS
<222> LOCATION: (1)..(396)
<223> OTHER INFORMATION: CBM

<400> SEQUENCE: 12

```
act agt aca tcc aaa gcc acc acc tcc tct tct tct tct gct gct         48
Thr Ser Thr Ser Lys Ala Thr Thr Ser Ser Ser Ser Ser Ala Ala
1               5                   10                  15 gct act act tct tca tca tgc acc gca aca agc acc acc ctc ccc atc    96
Ala Thr Thr Ser Ser Ser Cys Thr Ala Thr Ser Thr Thr Leu Pro Ile
                20                  25                  30 acc ttc gaa gaa ctc gtc acc act acc tac ggg gaa gaa gtc tac ctc   144
Thr Phe Glu Glu Leu Val Thr Thr Thr Tyr Gly Glu Glu Val Tyr Leu
            35                  40                  45 agc gga tct atc tcc cag ctc gga gag tgg gat acg agt gac gcg gtg   192
Ser Gly Ser Ile Ser Gln Leu Gly Glu Trp Asp Thr Ser Asp Ala Val
        50                  55                  60 aag ttg tcc gcg gat gat tat acc tcg agt aac ccc gag tgg tct gtt   240
Lys Leu Ser Ala Asp Asp Tyr Thr Ser Ser Asn Pro Glu Trp Ser Val
65                  70                  75                  80 act gtg tcg ttg ccg gtg ggg acg acc ttc gag tat aag ttt att aag   288
Thr Val Ser Leu Pro Val Gly Thr Thr Phe Glu Tyr Lys Phe Ile Lys
                85                  90                  95 gtc gat gag ggt gga agt gtg act tgg gaa agt gat ccg aat agg gag   336
Val Asp Glu Gly Gly Ser Val Thr Trp Glu Ser Asp Pro Asn Arg Glu
            100                 105                 110 tat act gtg cct gaa tgt ggg aat ggg agt ggg gag acg gtg gtt gat   384
Tyr Thr Val Pro Glu Cys Gly Asn Gly Ser Gly Glu Thr Val Val Asp
        115                 120                 125
```

```
acg tgg agg tag                                                            396
Thr Trp Arg
    130

<210> SEQ ID NO 13
<211> LENGTH: 131
<212> TYPE: PRT
<213> ORGANISM: Aspergillus kawachi

<400> SEQUENCE: 13

Thr Ser Thr Ser Lys Ala Thr Thr Ser Ser Ser Ser Ser Ala Ala
1               5                   10                  15

Ala Thr Thr Ser Ser Ser Cys Thr Ala Thr Ser Thr Thr Leu Pro Ile
            20                  25                  30

Thr Phe Glu Glu Leu Val Thr Thr Thr Tyr Gly Glu Glu Val Tyr Leu
        35                  40                  45

Ser Gly Ser Ile Ser Gln Leu Gly Glu Trp Asp Thr Ser Asp Ala Val
    50                  55                  60

Lys Leu Ser Ala Asp Asp Tyr Thr Ser Ser Asn Pro Glu Trp Ser Val
65                  70                  75                  80

Thr Val Ser Leu Pro Val Gly Thr Thr Phe Glu Tyr Lys Phe Ile Lys
                85                  90                  95

Val Asp Glu Gly Gly Ser Val Thr Trp Glu Ser Asp Pro Asn Arg Glu
            100                 105                 110

Tyr Thr Val Pro Glu Cys Gly Asn Gly Ser Gly Glu Thr Val Val Asp
        115                 120                 125

Thr Trp Arg
    130

<210> SEQ ID NO 14
<211> LENGTH: 102
<212> TYPE: PRT
<213> ORGANISM: Bacillus flavothermus
<220> FEATURE:
<221> NAME/KEY: MISC_FEATURE
<222> LOCATION: (1)..(102)
<223> OTHER INFORMATION: CBM

<400> SEQUENCE: 14

Ile Ser Thr Thr Ser Gln Ile Thr Phe Thr Val Asn Asn Ala Thr Thr
1               5                   10                  15

Val Trp Gly Gln Asn Val Tyr Val Val Gly Asn Ile Ser Gln Leu Gly
            20                  25                  30

Asn Trp Asp Pro Val His Ala Val Gln Met Thr Pro Ser Ser Tyr Pro
        35                  40                  45

Thr Trp Thr Val Thr Ile Pro Leu Leu Gln Gly Gln Asn Ile Gln Phe
    50                  55                  60

Lys Phe Ile Lys Lys Asp Ser Ala Gly Asn Val Ile Trp Glu Asp Ile
65                  70                  75                  80

Ser Asn Arg Thr Tyr Thr Val Pro Thr Ala Ala Ser Gly Ala Tyr Thr
                85                  90                  95

Ala Ser Trp Asn Val Pro
            100

<210> SEQ ID NO 15
<211> LENGTH: 99
<212> TYPE: PRT
<213> ORGANISM: Bacillus sp.
<220> FEATURE:
<221> NAME/KEY: MISC_FEATURE
<222> LOCATION: (1)..(99)
```

<223> OTHER INFORMATION: CBM

<400> SEQUENCE: 15

Thr Ser Asn Val Thr Phe Thr Val Asn Asn Ala Thr Thr Val Tyr Gly
1               5                   10                  15

Gln Asn Val Tyr Val Val Gly Asn Ile Pro Glu Leu Gly Asn Trp Asn
            20                  25                  30

Ile Ala Asn Ala Ile Gln Met Thr Pro Ser Ser Tyr Pro Thr Trp Lys
        35                  40                  45

Thr Thr Val Ser Leu Pro Gln Gly Lys Ala Ile Glu Phe Lys Phe Ile
    50                  55                  60

Lys Lys Asp Ser Ala Gly Asn Val Ile Trp Glu Asn Ile Ala Asn Arg
65                  70                  75                  80

Thr Tyr Thr Val Pro Phe Ser Ser Thr Gly Ser Tyr Thr Ala Asn Trp
                85                  90                  95

Asn Val Pro

<210> SEQ ID NO 16
<211> LENGTH: 102
<212> TYPE: PRT
<213> ORGANISM: Alcaliphilic Bacillus
<220> FEATURE:
<221> NAME/KEY: MISC_FEATURE
<222> LOCATION: (1)..(102)
<223> OTHER INFORMATION: CBM

<400> SEQUENCE: 16

Thr Ser Thr Thr Ser Gln Ile Thr Phe Thr Val Asn Asn Ala Thr Thr
1               5                   10                  15

Val Trp Gly Gln Asn Val Tyr Val Val Gly Asn Ile Ser Gln Leu Gly
            20                  25                  30

Asn Trp Asp Pro Val Asn Ala Val Gln Met Thr Pro Ser Ser Tyr Pro
        35                  40                  45

Thr Trp Val Val Thr Val Pro Leu Pro Gln Ser Gln Asn Ile Gln Phe
    50                  55                  60

Lys Phe Ile Lys Lys Asp Gly Ser Gly Asn Val Ile Trp Glu Asn Ile
65                  70                  75                  80

Ser Asn Arg Thr Tyr Thr Val Pro Thr Ala Ser Gly Ala Tyr Thr
                85                  90                  95

Ala Asn Trp Asn Val Pro
            100

<210> SEQ ID NO 17
<211> LENGTH: 112
<212> TYPE: PRT
<213> ORGANISM: Hormoconis resinae
<220> FEATURE:
<221> NAME/KEY: MISC_FEATURE
<222> LOCATION: (1)..(112)
<223> OTHER INFORMATION: CBM

<400> SEQUENCE: 17

Cys Gln Val Ser Ile Thr Phe Asn Ile Asn Ala Thr Thr Tyr Tyr Gly
1               5                   10                  15

Glu Asn Leu Tyr Val Ile Gly Asn Ser Ser Asp Leu Gly Ala Trp Asn
            20                  25                  30

Ile Ala Asp Ala Tyr Pro Leu Ser Ala Ser Tyr Thr Gln Asp Arg
        35                  40                  45

Pro Leu Trp Ser Ala Ala Ile Pro Leu Asn Ala Gly Glu Val Ile Ser
    50                  55                  60

```
Tyr Gln Tyr Val Arg Gln Glu Asp Cys Asp Gln Pro Tyr Ile Tyr Glu
 65                  70                  75                  80

Thr Val Asn Arg Thr Leu Thr Val Pro Ala Cys Gly Ala Ala Val
             85                  90                  95

Thr Thr Asp Asp Ala Trp Met Gly Pro Val Gly Ser Ser Gly Asn Cys
            100                 105                 110
```

<210> SEQ ID NO 18
<211> LENGTH: 95
<212> TYPE: PRT
<213> ORGANISM: Lentinula edodes
<220> FEATURE:
<221> NAME/KEY: MISC_FEATURE
<222> LOCATION: (1)..(95)
<223> OTHER INFORMATION: CBM

<400> SEQUENCE: 18

```
Val Ser Val Thr Phe Asn Val Asp Ala Ser Thr Leu Glu Gly Gln Asn
 1               5                  10                  15

Val Tyr Leu Thr Gly Ala Val Asp Ala Leu Glu Asp Trp Ser Thr Asp
             20                  25                  30

Asn Ala Ile Leu Leu Ser Ser Ala Asn Tyr Pro Thr Trp Ser Val Thr
             35                  40                  45

Val Asp Leu Pro Gly Ser Thr Asp Val Gln Tyr Lys Tyr Ile Lys Lys
         50                  55                  60

Asp Gly Ser Gly Thr Val Thr Trp Glu Ser Asp Pro Asn Met Glu Ile
 65                  70                  75                  80

Thr Thr Pro Ala Asn Gly Thr Tyr Ala Thr Asn Asp Thr Trp Arg
             85                  90                  95
```

<210> SEQ ID NO 19
<211> LENGTH: 107
<212> TYPE: PRT
<213> ORGANISM: Neurospora crassa
<220> FEATURE:
<221> NAME/KEY: MISC_FEATURE
<222> LOCATION: (1)..(107)
<223> OTHER INFORMATION: CBM

<400> SEQUENCE: 19

```
Cys Ala Ala Asp His Glu Val Leu Val Thr Phe Asn Glu Lys Val Thr
 1               5                  10                  15

Thr Ser Tyr Gly Gln Thr Val Lys Val Gly Ser Ile Ala Ala Leu
             20                  25                  30

Gly Asn Trp Ala Pro Ala Ser Gly Val Thr Leu Ser Ala Lys Gln Tyr
             35                  40                  45

Ser Ser Ser Asn Pro Leu Trp Ser Thr Thr Ile Ala Leu Pro Gln Gly
         50                  55                  60

Thr Ser Phe Lys Tyr Lys Tyr Val Val Val Asn Ser Asp Gly Ser Val
 65                  70                  75                  80

Lys Trp Glu Asn Asp Pro Asp Arg Ser Tyr Ala Val Gly Thr Asp Cys
             85                  90                  95

Ala Ser Thr Ala Thr Leu Asp Asp Thr Trp Arg
            100                 105
```

<210> SEQ ID NO 20
<211> LENGTH: 115
<212> TYPE: PRT
<213> ORGANISM: Talaromyces byssochlamydioides
<220> FEATURE:
<221> NAME/KEY: MISC_FEATURE

```
<222> LOCATION: (1)..(115)
<223> OTHER INFORMATION: CBM

<400> SEQUENCE: 20

Thr Thr Thr Gly Ala Ala Pro Cys Thr Thr Pro Thr Thr Val Ala Val
1               5                   10                  15

Thr Phe Asp Glu Ile Val Thr Thr Tyr Gly Glu Thr Val Tyr Leu
            20                  25                  30

Ser Gly Ser Ile Pro Ala Leu Gly Asn Trp Asp Thr Ser Ser Ala Ile
        35                  40                  45

Ala Leu Ser Ala Val Asp Tyr Thr Ser Ser Asn Pro Leu Trp Tyr Val
    50                  55                  60

Thr Val Asn Leu Pro Ala Gly Thr Ser Phe Glu Tyr Lys Phe Phe Val
65                  70                  75                  80

Gln Gln Thr Asp Gly Thr Ile Val Trp Glu Asp Pro Asn Arg Ser
            85                  90                  95

Tyr Thr Val Pro Ala Asn Cys Gly Gln Thr Thr Ala Ile Ile Asp Asp
            100                 105                 110

Ser Trp Gln
        115

<210> SEQ ID NO 21
<211> LENGTH: 115
<212> TYPE: PRT
<213> ORGANISM: Geosmithia cylindrospora
<220> FEATURE:
<221> NAME/KEY: MISC_FEATURE
<222> LOCATION: (1)..(115)
<223> OTHER INFORMATION: CBM

<400> SEQUENCE: 21

Thr Ser Thr Gly Ser Ala Pro Cys Thr Thr Pro Thr Thr Val Ala Val
1               5                   10                  15

Thr Phe Asp Glu Ile Val Thr Thr Ser Tyr Gly Glu Thr Val Tyr Leu
            20                  25                  30

Ala Gly Ser Ile Ala Ala Leu Gly Asn Trp Asp Thr Asn Ser Ala Ile
        35                  40                  45

Ala Leu Ser Ala Ala Asp Tyr Thr Ser Asn Asn Asn Leu Trp Tyr Val
    50                  55                  60

Thr Val Asn Leu Ala Ala Gly Thr Ser Phe Gln Tyr Lys Phe Phe Val
65                  70                  75                  80

Lys Glu Thr Asp Ser Thr Ile Val Trp Glu Asp Pro Asn Arg Ser
            85                  90                  95

Tyr Thr Val Pro Ala Asn Cys Gly Gln Thr Thr Ala Ile Ile Asp Asp
            100                 105                 110

Thr Trp Gln
        115

<210> SEQ ID NO 22
<211> LENGTH: 139
<212> TYPE: PRT
<213> ORGANISM: Scorias spongiosa CBM
<220> FEATURE:
<221> NAME/KEY: MISC_FEATURE
<222> LOCATION: (1)..(139)
<223> OTHER INFORMATION: CBM

<400> SEQUENCE: 22

Ala Lys Val Pro Ser Thr Cys Ser Ala Ser Ser Ala Thr Gly Thr Cys
1               5                   10                  15
```

```
Thr Thr Ala Thr Ser Thr Phe Gly Gly Ser Thr Pro Thr Thr Ser Cys
            20                  25                  30

Ala Thr Thr Pro Thr Leu Thr Val Leu Phe Asn Glu Arg Ala Thr
        35                  40                  45

Thr Asn Phe Gly Gln Asn Val His Leu Thr Gly Ser Ile Ser Gln Leu
 50                  55                  60

Gly Ser Trp Asp Thr Asp Ser Ala Val Ala Leu Ser Ala Val Asn Tyr
 65                  70                  75                  80

Thr Ser Ser Asp Pro Leu Trp Phe Val Arg Val Gln Leu Pro Ala Gly
                 85                  90                  95

Thr Ser Phe Gln Tyr Lys Tyr Phe Lys Lys Asp Ser Ser Asn Ala Val
                100                 105                 110

Ala Trp Glu Ser Asp Pro Asn Arg Ser Tyr Thr Val Pro Leu Asn Cys
        115                 120                 125

Ala Gly Thr Ala Thr Glu Asn Asp Thr Trp Arg
    130                 135
```

<210> SEQ ID NO 23
<211> LENGTH: 126
<212> TYPE: PRT
<213> ORGANISM: Eupenicillium ludwigii
<220> FEATURE:
<221> NAME/KEY: MISC_FEATURE
<222> LOCATION: (1)..(126)
<223> OTHER INFORMATION: CBM

<400> SEQUENCE: 23

```
Ser Thr Thr Thr Thr Ser Thr Thr Lys Thr Thr Thr Ser Thr Thr
 1               5                  10                  15

Thr Ser Cys Thr Thr Pro Thr Ala Val Ala Val Thr Phe Asp Leu Ile
            20                  25                  30

Ala Thr Thr Tyr Tyr Gly Glu Asn Ile Lys Ile Ala Gly Ser Ile Ser
        35                  40                  45

Gln Leu Gly Asp Trp Asp Thr Ser Asn Ala Val Ala Leu Ser Ala Ala
 50                  55                  60

Asp Tyr Thr Ser Ser Asp His Leu Trp Phe Val Asp Ile Asp Leu Pro
 65                  70                  75                  80

Ala Gly Thr Val Phe Glu Tyr Lys Tyr Ile Arg Ile Glu Ser Asp Gly
                 85                  90                  95

Ser Ile Glu Trp Glu Ser Asp Pro Asn Arg Ser Tyr Thr Val Pro Ala
                100                 105                 110

Ala Cys Ala Thr Thr Ala Val Thr Glu Asn Asp Thr Trp Arg
        115                 120                 125
```

<210> SEQ ID NO 24
<211> LENGTH: 116
<212> TYPE: PRT
<213> ORGANISM: Aspergillus japonicus
<220> FEATURE:
<221> NAME/KEY: MISC_FEATURE
<222> LOCATION: (1)..(116)
<223> OTHER INFORMATION: CBM

<400> SEQUENCE: 24

```
Lys Thr Ser Thr Thr Ser Ser Cys Ser Thr Pro Thr Ser Val Ala
 1               5                  10                  15

Val Thr Phe Asp Val Ile Ala Thr Thr Thr Tyr Gly Glu Asn Val Tyr
            20                  25                  30

Ile Ser Gly Ser Ile Ser Gln Leu Gly Ser Trp Asp Thr Ser Ser Ala
        35                  40                  45
```

```
Ile Ala Leu Ser Ala Ser Gln Tyr Thr Ser Ser Asn Asn Leu Trp Tyr
 50                  55                  60

Ala Thr Val His Leu Pro Ala Gly Thr Phe Gln Tyr Lys Tyr Ile
 65                  70                  75                  80

Arg Lys Glu Thr Asp Gly Ser Val Thr Trp Glu Ser Asp Pro Asn Arg
                 85                  90                  95

Ser Tyr Thr Val Pro Ser Ser Cys Gly Val Ser Ser Ala Thr Glu Ser
                100                 105                 110

Asp Thr Trp Arg
        115

<210> SEQ ID NO 25
<211> LENGTH: 133
<212> TYPE: PRT
<213> ORGANISM: Penicillium cf. miczynskii
<220> FEATURE:
<221> NAME/KEY: MISC_FEATURE
<222> LOCATION: (1)..(133)
<223> OTHER INFORMATION: CBM

<400> SEQUENCE: 25

Thr Thr Thr Gly Gly Thr Thr Thr Ser Gln Gly Ser Thr Thr Thr
 1               5                  10                  15

Ser Lys Thr Ser Thr Thr Thr Ser Ser Cys Thr Ala Pro Thr Ser Val
                 20                  25                  30

Ala Val Thr Phe Asp Leu Ile Ala Thr Thr Val Tyr Asp Glu Asn Val
                 35                  40                  45

Gln Leu Ala Gly Ser Ile Ser Ala Leu Gly Ser Trp Asp Thr Ser Ser
 50                  55                  60

Ala Ile Arg Leu Ser Ala Ser Gln Tyr Thr Ser Ser Asn His Leu Trp
 65                  70                  75                  80

Tyr Val Ala Val Ser Leu Pro Ala Gly Gln Val Phe Gln Tyr Lys Tyr
                 85                  90                  95

Ile Arg Val Ala Ser Ser Gly Thr Ile Thr Trp Glu Ser Asp Pro Asn
                100                 105                 110

Leu Ser Tyr Thr Val Pro Val Ala Cys Ala Ala Thr Ala Val Thr Ile
                115                 120                 125

Ser Asp Thr Trp Arg
        130

<210> SEQ ID NO 26
<211> LENGTH: 116
<212> TYPE: PRT
<213> ORGANISM: Mz1 Penicillium sp.
<220> FEATURE:
<221> NAME/KEY: MISC_FEATURE
<222> LOCATION: (1)..(116)
<223> OTHER INFORMATION: CBM

<400> SEQUENCE: 26

Thr Lys Thr Ser Thr Ser Thr Ser Cys Thr Thr Pro Thr Ala Val Ala
 1               5                  10                  15

Val Thr Phe Asp Leu Ile Ala Thr Thr Thr Tyr Gly Glu Asn Ile Lys
                 20                  25                  30

Ile Ala Gly Ser Ile Ala Ala Leu Gly Ala Trp Asp Thr Asp Ala
                 35                  40                  45

Val Ala Leu Ser Ala Ala Asp Tyr Thr Asp Ser Asp His Leu Trp Phe
 50                  55                  60

Val Thr Gln Ser Ile Pro Ala Gly Thr Val Phe Glu Tyr Lys Tyr Ile
```

```
                65                  70                  75                  80
Arg Val Glu Ser Asp Gly Thr Ile Glu Trp Glu Ser Asp Pro Asn Arg
                85                  90                  95

Ser Tyr Thr Val Pro Ala Ala Cys Ala Thr Thr Ala Val Thr Glu Ser
            100                 105                 110

Asp Thr Trp Arg
        115

<210> SEQ ID NO 27
<211> LENGTH: 114
<212> TYPE: PRT
<213> ORGANISM: Thysanophora sp.
<220> FEATURE:
<221> NAME/KEY: MISC_FEATURE
<222> LOCATION: (1)..(114)
<223> OTHER INFORMATION: CBM

<400> SEQUENCE: 27

Phe Thr Ser Thr Thr Lys Thr Ser Cys Thr Thr Pro Thr Ser Val Ala
1               5                  10                  15

Val Thr Phe Asp Leu Ile Ala Thr Thr Thr Tyr Gly Glu Ser Ile Arg
            20                  25                  30

Leu Val Gly Ser Ile Ser Glu Leu Gly Asp Trp Asp Thr Gly Ser Ala
        35                  40                  45

Ile Ala Leu His Ala Thr Asp Tyr Thr Asp Ser Asp His Leu Trp Phe
50                  55                  60

Val Thr Val Gly Leu Pro Ala Gly Ala Ser Phe Glu Tyr Lys Tyr Ile
65                  70                  75                  80

Arg Val Glu Ser Ser Gly Thr Ile Glu Trp Glu Ser Asp Pro Asn Arg
                85                  90                  95

Ser Tyr Thr Val Pro Ala Ala Cys Ala Thr Thr Ala Val Thr Glu Ser
            100                 105                 110

Asp Thr

<210> SEQ ID NO 28
<211> LENGTH: 111
<212> TYPE: PRT
<213> ORGANISM: Humicola grisea var. thermoidea
<220> FEATURE:
<221> NAME/KEY: MISC_FEATURE
<222> LOCATION: (1)..(111)
<223> OTHER INFORMATION: CBM

<400> SEQUENCE: 28

Ala Asp Ala Ser Glu Val Tyr Val Thr Phe Asn Glu Arg Val Ser Thr
1               5                  10                  15

Ala Trp Gly Glu Thr Ile Lys Val Val Gly Asn Val Pro Ala Leu Gly
            20                  25                  30

Asn Trp Asp Thr Ser Lys Ala Val Thr Leu Ser Ala Ser Gly Tyr Lys
        35                  40                  45

Ser Asn Asp Pro Leu Trp Ser Ile Thr Val Pro Ile Lys Ala Thr Gly
50                  55                  60

Ser Ala Val Gln Tyr Lys Tyr Ile Lys Val Gly Thr Asn Gly Lys Ile
65                  70                  75                  80

Thr Trp Glu Ser Asp Pro Asn Arg Ser Ile Thr Leu Gln Thr Ala Ser
                85                  90                  95

Ser Ala Gly Lys Cys Ala Ala Gln Thr Val Asn Asp Ser Trp Arg
            100                 105                 110
```

```
<210> SEQ ID NO 29
<211> LENGTH: 108
<212> TYPE: PRT
<213> ORGANISM: Aspergillus niger
<220> FEATURE:
<221> NAME/KEY: MISC_FEATURE
<222> LOCATION: (1)..(108)
<223> OTHER INFORMATION: CBM

<400> SEQUENCE: 29

Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
            20                  25                  30

Gly Asp Trp Glu Thr Ser Asp Gly Ile Ala Leu Ser Ala Asp Lys Tyr
        35                  40                  45

Thr Ser Ser Asp Pro Leu Trp Tyr Val Thr Val Thr Leu Pro Ala Gly
    50                  55                  60

Glu Ser Phe Glu Tyr Lys Phe Ile Arg Ile Glu Ser Asp Asp Ser Val
65                  70                  75                  80

Glu Trp Glu Ser Asp Pro Asn Arg Glu Tyr Thr Val Pro Gln Ala Cys
                85                  90                  95

Gly Thr Ser Thr Ala Thr Val Thr Asp Thr Trp Arg
            100                 105

<210> SEQ ID NO 30
<211> LENGTH: 97
<212> TYPE: PRT
<213> ORGANISM: Athelia rolfsii
<220> FEATURE:
<221> NAME/KEY: MISC_FEATURE
<222> LOCATION: (1)..(97)
<223> OTHER INFORMATION: CBM

<400> SEQUENCE: 30

Val Glu Val Thr Phe Asp Val Tyr Ala Thr Thr Val Tyr Gly Gln Asn
1               5                   10                  15

Ile Tyr Ile Thr Gly Asp Val Ser Glu Leu Gly Asn Trp Thr Pro Ala
            20                  25                  30

Asn Gly Val Ala Leu Ser Ser Ala Asn Tyr Pro Thr Trp Ser Ala Thr
        35                  40                  45

Ile Ala Leu Pro Ala Asp Thr Thr Ile Gln Tyr Lys Tyr Val Asn Ile
    50                  55                  60

Asp Gly Ser Thr Val Ile Trp Glu Asp Ala Ile Ser Asn Arg Glu Ile
65                  70                  75                  80

Thr Thr Pro Ala Ser Gly Thr Tyr Thr Glu Lys Asp Thr Trp Asp Glu
                85                  90                  95

Ser

<210> SEQ ID NO 31
<211> LENGTH: 640
<212> TYPE: PRT
<213> ORGANISM: Aspergillus kawachi alpha-amylase
<220> FEATURE:
<221> NAME/KEY: mat_peptide
<222> LOCATION: (22)..(640)

<400> SEQUENCE: 31

Met Arg Val Ser Thr Ser Ser Ile Ala Leu Ala Val Ser Leu Phe Gly
        -20                 -15                 -10

Lys Leu Ala Leu Gly Leu Ser Ala Ala Glu Trp Arg Thr Gln Ser Ile
    -5              -1  1               5                   10
```

```
Tyr Phe Leu Leu Thr Asp Arg Phe Gly Arg Thr Asp Asn Ser Thr Thr
                15                  20                  25
Ala Thr Cys Asn Thr Gly Asp Gln Ile Tyr Cys Gly Gly Ser Trp Gln
                30                  35                  40
Gly Ile Ile Asn His Leu Asp Tyr Ile Gln Gly Met Gly Phe Thr Ala
                45                  50                  55
Ile Trp Ile Ser Pro Ile Thr Glu Gln Leu Pro Gln Asp Thr Ser Asp
60                  65                  70                  75
Gly Glu Ala Tyr His Gly Tyr Trp Gln Gln Lys Ile Tyr Tyr Val Asn
                80                  85                  90
Ser Asn Phe Gly Thr Ala Asp Asp Leu Lys Ser Leu Ser Asp Ala Leu
                95                  100                 105
His Ala Arg Gly Met Tyr Leu Met Val Asp Val Val Pro Asn His Met
                110                 115                 120
Gly Tyr Ala Gly Asn Gly Asn Asp Val Asp Tyr Ser Val Phe Asp Pro
                125                 130                 135
Phe Asp Ser Ser Ser Tyr Phe His Pro Tyr Cys Leu Ile Thr Asp Trp
140                 145                 150                 155
Asp Asn Leu Thr Met Val Gln Asp Cys Trp Glu Gly Asp Thr Ile Val
                160                 165                 170
Ser Leu Pro Asp Leu Asn Thr Thr Glu Thr Ala Val Arg Thr Ile Trp
                175                 180                 185
Tyr Asp Trp Val Ala Asp Leu Val Ser Asn Tyr Ser Val Asp Gly Leu
                190                 195                 200
Arg Ile Asp Ser Val Glu Glu Val Glu Pro Asp Phe Phe Pro Gly Tyr
                205                 210                 215
Gln Glu Ala Ala Gly Val Tyr Cys Val Gly Glu Val Asp Asn Gly Asn
220                 225                 230                 235
Pro Ala Leu Asp Cys Pro Tyr Gln Lys Tyr Leu Asp Gly Val Leu Asn
                240                 245                 250
Tyr Pro Ile Tyr Trp Gln Leu Leu Tyr Ala Phe Glu Ser Ser Ser Gly
                255                 260                 265
Ser Ile Ser Asn Leu Tyr Asn Met Ile Lys Ser Val Ala Ser Asp Cys
                270                 275                 280
Ser Asp Pro Thr Leu Leu Gly Asn Phe Ile Glu Asn His Asp Asn Pro
                285                 290                 295
Arg Phe Ala Ser Tyr Thr Ser Asp Tyr Ser Gln Ala Lys Asn Val Leu
300                 305                 310                 315
Ser Tyr Ile Phe Leu Ser Asp Gly Ile Pro Ile Val Tyr Ala Gly Glu
                320                 325                 330
Glu Gln His Tyr Ser Gly Gly Asp Val Pro Tyr Asn Arg Glu Ala Thr
                335                 340                 345
Trp Leu Ser Gly Tyr Asp Thr Ser Ala Glu Leu Tyr Thr Trp Ile Ala
                350                 355                 360
Thr Thr Asn Ala Ile Arg Lys Leu Ala Ile Ser Ala Asp Ser Asp Tyr
                365                 370                 375
Ile Thr Tyr Lys Asn Asp Pro Ile Tyr Thr Asp Ser Asn Thr Ile Ala
380                 385                 390                 395
Met Arg Lys Gly Thr Ser Gly Ser Gln Ile Ile Thr Val Leu Ser Asn
                400                 405                 410
Lys Gly Ser Ser Gly Ser Ser Tyr Thr Leu Thr Leu Ser Gly Ser Gly
                415                 420                 425
Tyr Thr Ser Gly Thr Lys Leu Ile Glu Ala Tyr Thr Cys Thr Ser Val
```

-continued

```
                   430                 435                 440
Thr Val Asp Ser Asn Gly Asp Ile Pro Val Pro Met Ala Ser Gly Leu
    445                 450                 455

Pro Arg Val Leu Leu Pro Ala Ser Val Val Asp Ser Ser Ser Leu Cys
460                 465                 470                 475

Gly Gly Ser Gly Asn Thr Thr Thr Thr Thr Ala Ala Thr Ser Thr
                480                 485                 490

Ser Lys Ala Thr Thr Ser Ser Ser Ser Ser Ala Ala Ala Thr Thr
                495                 500                 505

Ser Ser Ser Cys Thr Ala Thr Ser Thr Thr Leu Pro Ile Thr Phe Glu
        510                 515                 520

Glu Leu Val Thr Thr Thr Tyr Gly Glu Glu Val Tyr Leu Ser Gly Ser
    525                 530                 535

Ile Ser Gln Leu Gly Glu Trp His Thr Ser Asp Ala Val Lys Leu Ser
540                 545                 550                 555

Ala Asp Asp Tyr Thr Ser Ser Asn Pro Glu Trp Ser Val Thr Val Ser
                560                 565                 570

Leu Pro Val Gly Thr Thr Phe Glu Tyr Lys Phe Ile Lys Val Asp Glu
                575                 580                 585

Gly Gly Ser Val Thr Trp Glu Ser Asp Pro Asn Arg Glu Tyr Thr Val
                590                 595                 600

Pro Glu Cys Gly Ser Gly Ser Gly Glu Thr Val Val Asp Thr Trp Arg
    605                 610                 615

<210> SEQ ID NO 32
<211> LENGTH: 1860
<212> TYPE: DNA
<213> ORGANISM: Artificial
<220> FEATURE:
<223> OTHER INFORMATION: hybrid consisting of Aspergillus niger acid
      alpha-amylase catalytic domain-Aspergillus kawachii alpha-amylase
      linker-Aspergillus niger glucoamylase CBM
<220> FEATURE:
<221> NAME/KEY: CDS
<222> LOCATION: (1)..(1860)
<223> OTHER INFORMATION: hybrid

<400> SEQUENCE: 32 ctg tcg gct gca gaa tgg cgc act cag tcg att tac ttc cta ttg acg      48
Leu Ser Ala Ala Glu Trp Arg Thr Gln Ser Ile Tyr Phe Leu Leu Thr
1               5                   10                  15 gat cgg ttc ggt agg acg gac aat tcg acg aca gct aca tgc gat acg      96
Asp Arg Phe Gly Arg Thr Asp Asn Ser Thr Thr Ala Thr Cys Asp Thr
            20                  25                  30 ggt gac caa atc tat tgt ggt ggc agt tgg caa gga atc atc aac cat     144
Gly Asp Gln Ile Tyr Cys Gly Gly Ser Trp Gln Gly Ile Ile Asn His
        35                  40                  45 ctg gat tat atc cag ggc atg gga ttc acg gcc atc tgg atc tcg cct     192
Leu Asp Tyr Ile Gln Gly Met Gly Phe Thr Ala Ile Trp Ile Ser Pro
    50                  55                  60 atc act gaa cag ctg ccc cag gat act gct gat ggt gaa gct tac cat     240
Ile Thr Glu Gln Leu Pro Gln Asp Thr Ala Asp Gly Glu Ala Tyr His
65                  70                  75                  80 gga tat tgg cag cag aag ata tac gac gtg aac tcc aac ttc ggc act     288
Gly Tyr Trp Gln Gln Lys Ile Tyr Asp Val Asn Ser Asn Phe Gly Thr
                85                  90                  95 gca gat gac ctc aag tcc ctc tca gat gcg ctt cat gcc cgc gga atg     336
Ala Asp Asp Leu Lys Ser Leu Ser Asp Ala Leu His Ala Arg Gly Met
            100                 105                 110 tac ctc atg gtg gac gtc gtc cct aac cac atg ggc tac gcc ggc aac     384
```

```
Tyr Leu Met Val Asp Val Val Pro Asn His Met Gly Tyr Ala Gly Asn
        115                 120                 125 ggc aac gat gta gac tac agc gtc ttc gac ccc ttc gat tcc tcc tcc    432
Gly Asn Asp Val Asp Tyr Ser Val Phe Asp Pro Phe Asp Ser Ser Ser
130                 135                 140 tac ttc cac cca tac tgc ctg atc aca gat tgg gac aac ttg acc atg    480
Tyr Phe His Pro Tyr Cys Leu Ile Thr Asp Trp Asp Asn Leu Thr Met
145                 150                 155                 160 gtc caa gat tgt tgg gag ggt gac acc atc gta tct ctg cca gac cta    528
Val Gln Asp Cys Trp Glu Gly Asp Thr Ile Val Ser Leu Pro Asp Leu
                165                 170                 175 aac acc acc gaa act gcc gtg aga aca atc tgg tat gac tgg gta gcc    576
Asn Thr Thr Glu Thr Ala Val Arg Thr Ile Trp Tyr Asp Trp Val Ala
            180                 185                 190 gac ctg gta tcc aat tat tca gtc gac gga ctc cgc atc gac agt gtc    624
Asp Leu Val Ser Asn Tyr Ser Val Asp Gly Leu Arg Ile Asp Ser Val
        195                 200                 205 ctc gaa gtc gaa cca gac ttc ttc ccg ggc tac cag gaa gca gca ggt    672
Leu Glu Val Glu Pro Asp Phe Phe Pro Gly Tyr Gln Glu Ala Ala Gly
210                 215                 220 gtc tac tgc gtc ggc gaa gtc gac aac ggc aac cct gcc ctc gac tgc    720
Val Tyr Cys Val Gly Glu Val Asp Asn Gly Asn Pro Ala Leu Asp Cys
225                 230                 235                 240 cca tac cag aag gtc ctg gac ggc gtc ctc aac tat ccg atc tac tgg    768
Pro Tyr Gln Lys Val Leu Asp Gly Val Leu Asn Tyr Pro Ile Tyr Trp
                245                 250                 255 caa ctc ctc tac gcc ttc gaa tcc tcc agc ggc agc atc agc aat ctc    816
Gln Leu Leu Tyr Ala Phe Glu Ser Ser Ser Gly Ser Ile Ser Asn Leu
            260                 265                 270 tac aac atg atc aaa tcc gtc gca agc gac tgc tcc gat ccg aca cta    864
Tyr Asn Met Ile Lys Ser Val Ala Ser Asp Cys Ser Asp Pro Thr Leu
        275                 280                 285 ctc ggc aac ttc atc gaa aac cac gac aat ccc cgt ttc gcc tcc tac    912
Leu Gly Asn Phe Ile Glu Asn His Asp Asn Pro Arg Phe Ala Ser Tyr
290                 295                 300 acc tcc gac tac tcg caa gcc aaa aac gtc ctc agc tac atc ttc ctc    960
Thr Ser Asp Tyr Ser Gln Ala Lys Asn Val Leu Ser Tyr Ile Phe Leu
305                 310                 315                 320 tcc gac ggc atc ccc atc gtc tac gcc ggc gaa gaa cag cac tac tcc   1008
Ser Asp Gly Ile Pro Ile Val Tyr Ala Gly Glu Glu Gln His Tyr Ser
                325                 330                 335 ggc ggc aag gtg ccc tac aac cgc gaa gcg acc tgg ctt tca ggc tac   1056
Gly Gly Lys Val Pro Tyr Asn Arg Glu Ala Thr Trp Leu Ser Gly Tyr
            340                 345                 350 gac acc tcc gca gag ctg tac acc tgg ata gcc acc acg aac gcg atc   1104
Asp Thr Ser Ala Glu Leu Tyr Thr Trp Ile Ala Thr Thr Asn Ala Ile
        355                 360                 365 cgc aaa cta gcc atc tca gct gac tcg gcc tac att acc tac gcg aat   1152
Arg Lys Leu Ala Ile Ser Ala Asp Ser Ala Tyr Ile Thr Tyr Ala Asn
370                 375                 380 gat gca ttc tac act gac agc aac acc atc gca atg cgc aaa ggc acc   1200
Asp Ala Phe Tyr Thr Asp Ser Asn Thr Ile Ala Met Arg Lys Gly Thr
385                 390                 395                 400 tca ggg agc caa gtc atc acc gtc ctc tcc aac aaa ggc tcc tca gga   1248
Ser Gly Ser Gln Val Ile Thr Val Leu Ser Asn Lys Gly Ser Ser Gly
                405                 410                 415 agc agc tac acc ctg acc ctc agc gga agc ggc tac aca tcc ggc acg   1296
Ser Ser Tyr Thr Leu Thr Leu Ser Gly Ser Gly Tyr Thr Ser Gly Thr
            420                 425                 430 aag ctg atc gaa gcg tac aca tgc aca tcc gtg acc gtg gac tcg agc   1344
Lys Leu Ile Glu Ala Tyr Thr Cys Thr Ser Val Thr Val Asp Ser Ser
```

```
Lys Leu Ile Glu Ala Tyr Thr Cys Thr Ser Val Thr Val Asp Ser Ser
        435                 440                 445 ggc gat att ccc gtg ccg atg gcg tcg gga tta ccg aga gtt ctt ctg    1392
Gly Asp Ile Pro Val Pro Met Ala Ser Gly Leu Pro Arg Val Leu Leu
450                 455                 460 ccc gcg tcc gtc gtc gat agc tct tcg ctc tgt ggc ggg agc gga aga    1440
Pro Ala Ser Val Val Asp Ser Ser Ser Leu Cys Gly Gly Ser Gly Arg
465                 470                 475                 480 aca acc acg acc aca act gct gct gct act agt aca tcc aaa gcc acc    1488
Thr Thr Thr Thr Thr Thr Ala Ala Ala Thr Ser Thr Ser Lys Ala Thr
                    485                 490                 495 acc tcc tct tct tct tct tct gct gct gct act act tct tca tca tgt    1536
Thr Ser Ser Ser Ser Ser Ser Ala Ala Ala Thr Thr Ser Ser Ser Cys
                500                 505                 510 acc act ccc acc gcc gtg gct gtg act ttc gat ctg aca gct acc acc    1584
Thr Thr Pro Thr Ala Val Ala Val Thr Phe Asp Leu Thr Ala Thr Thr
            515                 520                 525 acc tac ggc gag aac atc tac ctg gtc gga tcg atc tct cag ctg ggt    1632
Thr Tyr Gly Glu Asn Ile Tyr Leu Val Gly Ser Ile Ser Gln Leu Gly
        530                 535                 540 gac tgg gaa acc agc gac ggc ata gct ctg agt gct gac aag tac act    1680
Asp Trp Glu Thr Ser Asp Gly Ile Ala Leu Ser Ala Asp Lys Tyr Thr
545                 550                 555                 560 tcc agc gac ccg ctc tgg tat gtc act gtg act ctg ccg gct ggt gag    1728
Ser Ser Asp Pro Leu Trp Tyr Val Thr Val Thr Leu Pro Ala Gly Glu
                    565                 570                 575 tcg ttt gag tac aag ttt atc cgc att gag agc gat gac tcc gtg gag    1776
Ser Phe Glu Tyr Lys Phe Ile Arg Ile Glu Ser Asp Asp Ser Val Glu
                580                 585                 590 tgg gag agt gat ccc aac cga gaa tac acc gtt cct cag gcg tgc gga    1824
Trp Glu Ser Asp Pro Asn Arg Glu Tyr Thr Val Pro Gln Ala Cys Gly
            595                 600                 605 acg tcg acc gcg acg gtg act gac acc tgg cgg tag                    1860
Thr Ser Thr Ala Thr Val Thr Asp Thr Trp Arg
        610                 615

<210> SEQ ID NO 33
<211> LENGTH: 619
<212> TYPE: PRT
<213> ORGANISM: Artificial
<220> FEATURE:
<223> OTHER INFORMATION: Synthetic Construct

<400> SEQUENCE: 33

Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asp Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
    50                  55                  60

Ile Thr Glu Gln Leu Pro Gln Asp Thr Ala Asp Gly Glu Ala Tyr His
65                  70                  75                  80

Gly Tyr Trp Gln Gln Lys Ile Tyr Asp Val Asn Ser Asn Phe Gly Thr
                85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
        115                 120                 125
```

```
Gly Asn Asp Val Asp Tyr Ser Val Phe Asp Pro Phe Asp Ser Ser
            130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
                165                 170                 175

Asn Thr Thr Glu Thr Ala Val Arg Thr Ile Trp Tyr Asp Trp Val Ala
                180                 185                 190

Asp Leu Val Ser Asn Tyr Ser Val Asp Gly Leu Arg Ile Asp Ser Val
                195                 200                 205

Leu Glu Val Glu Pro Asp Phe Phe Pro Gly Tyr Gln Glu Ala Ala Gly
            210                 215                 220

Val Tyr Cys Val Gly Glu Val Asp Asn Gly Asn Pro Ala Leu Asp Cys
225                 230                 235                 240

Pro Tyr Gln Lys Val Leu Asp Gly Val Leu Asn Tyr Pro Ile Tyr Trp
                245                 250                 255

Gln Leu Leu Tyr Ala Phe Glu Ser Ser Gly Ser Ile Ser Asn Leu
            260                 265                 270

Tyr Asn Met Ile Lys Ser Val Ala Ser Asp Cys Ser Asp Pro Thr Leu
            275                 280                 285

Leu Gly Asn Phe Ile Glu Asn His Asp Asn Pro Arg Phe Ala Ser Tyr
            290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Gln His Tyr Ser
                325                 330                 335

Gly Gly Lys Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
            355                 360                 365

Arg Lys Leu Ala Ile Ser Ala Asp Ser Ala Tyr Ile Thr Tyr Ala Asn
370                 375                 380

Asp Ala Phe Tyr Thr Asp Ser Asn Thr Ile Ala Met Arg Lys Gly Thr
385                 390                 395                 400

Ser Gly Ser Gln Val Ile Thr Val Leu Ser Asn Lys Gly Ser Ser Gly
                405                 410                 415

Ser Ser Tyr Thr Leu Thr Leu Ser Gly Ser Gly Tyr Thr Ser Gly Thr
            420                 425                 430

Lys Leu Ile Glu Ala Tyr Thr Cys Thr Ser Val Thr Val Asp Ser Ser
            435                 440                 445

Gly Asp Ile Pro Val Pro Met Ala Ser Gly Leu Pro Arg Val Leu Leu
            450                 455                 460

Pro Ala Ser Val Val Asp Ser Ser Ser Leu Cys Gly Gly Ser Gly Arg
465                 470                 475                 480

Thr Thr Thr Thr Thr Thr Ala Ala Ala Thr Ser Thr Ser Lys Ala Thr
                485                 490                 495

Thr Ser Ser Ser Ser Ser Ser Ala Ala Ala Thr Thr Ser Ser Ser Cys
            500                 505                 510

Thr Thr Pro Thr Ala Val Ala Val Thr Phe Asp Leu Thr Ala Thr Thr
            515                 520                 525

Thr Tyr Gly Glu Asn Ile Tyr Leu Val Gly Ser Ile Ser Gln Leu Gly
            530                 535                 540

Asp Trp Glu Thr Ser Asp Gly Ile Ala Leu Ser Ala Asp Lys Tyr Thr
```

Ser Ser Asp Pro Leu Trp Tyr Val Thr Val Thr Leu Pro Ala Gly Glu
545                 550                 555                 560

Ser Phe Glu Tyr Lys Phe Ile Arg Ile Glu Ser Asp Asp Ser Val Glu
            565                 570                 575

Trp Glu Ser Asp Pro Asn Arg Glu Tyr Thr Val Pro Gln Ala Cys Gly
        580                 585                 590

Thr Ser Thr Ala Thr Val Thr Asp Thr Trp Arg
    595                 600                 605

610                 615

<210> SEQ ID NO 34
<211> LENGTH: 1827
<212> TYPE: DNA
<213> ORGANISM: Artificial sequence
<220> FEATURE:
<223> OTHER INFORMATION: Hybrid containing Aspergillus niger acid
      alpha-amylase catalytic domain-Aspergillus kawachii alpha-amylase
      linker-Athelia rolfsii glucoamylase CBD
<220> FEATURE:
<221> NAME/KEY: CDS
<222> LOCATION: (1)..(1827)
<223> OTHER INFORMATION: Hybrid

<400> SEQUENCE: 34

| ctg tcg gct gca gaa tgg cgc act cag tcg att tac ttc cta ttg acg | 48 |
|---|---|
| Leu Ser Ala Ala Glu Trp Arg Thr Gln Ser Ile Tyr Phe Leu Leu Thr | |
| 1               5                   10                  15 | |

| gat cgg ttc ggt agg acg gac aat tcg acg aca gct aca tgc gat acg | 96 |
|---|---|
| Asp Arg Phe Gly Arg Thr Asp Asn Ser Thr Thr Ala Thr Cys Asp Thr | |
|                 20                  25                  30 | |

| ggt gac caa atc tat tgt ggt ggc agt tgg caa gga atc atc aac cat | 144 |
|---|---|
| Gly Asp Gln Ile Tyr Cys Gly Gly Ser Trp Gln Gly Ile Ile Asn His | |
|             35                  40                  45 | |

| ctg gat tat atc cag ggc atg gga ttc acg gcc atc tgg atc tcg cct | 192 |
|---|---|
| Leu Asp Tyr Ile Gln Gly Met Gly Phe Thr Ala Ile Trp Ile Ser Pro | |
|         50                  55                  60 | |

| atc act gaa cag ctg ccc cag gat act gct gat ggt gaa gct tac cat | 240 |
|---|---|
| Ile Thr Glu Gln Leu Pro Gln Asp Thr Ala Asp Gly Glu Ala Tyr His | |
| 65                  70                  75                  80 | |

| gga tat tgg cag cag aag ata tac gac gtg aac tcc aac ttc ggc act | 288 |
|---|---|
| Gly Tyr Trp Gln Gln Lys Ile Tyr Asp Val Asn Ser Asn Phe Gly Thr | |
|                 85                  90                  95 | |

| gca gat gac ctc aag tcc ctc tca gat gcg ctt cat gcc cgc gga atg | 336 |
|---|---|
| Ala Asp Asp Leu Lys Ser Leu Ser Asp Ala Leu His Ala Arg Gly Met | |
|                 100                 105                 110 | |

| tac ctc atg gtg gac gtc gtc cct aac cac atg ggc tac gcc ggc aac | 384 |
|---|---|
| Tyr Leu Met Val Asp Val Val Pro Asn His Met Gly Tyr Ala Gly Asn | |
|             115                 120                 125 | |

| ggc aac gat gta gac tac agc gtc ttc gac ccc ttc gat tcc tcc tcc | 432 |
|---|---|
| Gly Asn Asp Val Asp Tyr Ser Val Phe Asp Pro Phe Asp Ser Ser Ser | |
|         130                 135                 140 | |

| tac ttc cac cca tac tgc ctg atc aca gat tgg gac aac ttg acc atg | 480 |
|---|---|
| Tyr Phe His Pro Tyr Cys Leu Ile Thr Asp Trp Asp Asn Leu Thr Met | |
| 145                 150                 155                 160 | |

| gtc caa gat tgt tgg gag ggt gac acc atc gta tct ctg cca gac cta | 528 |
|---|---|
| Val Gln Asp Cys Trp Glu Gly Asp Thr Ile Val Ser Leu Pro Asp Leu | |
|                 165                 170                 175 | |

| aac acc acc gaa act gcc gtg aga aca atc tgg tat gac tgg gta gcc | 576 |
|---|---|
| Asn Thr Thr Glu Thr Ala Val Arg Thr Ile Trp Tyr Asp Trp Val Ala | |
|                 180                 185                 190 | |

| gac ctg gta tcc aat tat tca gtc gac gga ctc cgc atc gac agt gtc | 624 |
|---|---|
| Asp Leu Val Ser Asn Tyr Ser Val Asp Gly Leu Arg Ile Asp Ser Val | |

-continued

|     |     |     | 195 |     |     |     | 200 |     |     |     | 205 |     |     |     |      |
|-----|-----|-----|-----|-----|-----|-----|-----|-----|-----|-----|-----|-----|-----|-----|------|

```
ctc gaa gtc gaa cca gac ttc ttc ccg ggc tac cag gaa gca gca ggt     672
Leu Glu Val Glu Pro Asp Phe Phe Pro Gly Tyr Gln Glu Ala Ala Gly
210                 215                 220 gtc tac tgc gtc ggc gaa gtc gac aac ggc aac cct gcc ctc gac tgc     720
Val Tyr Cys Val Gly Glu Val Asp Asn Gly Asn Pro Ala Leu Asp Cys
225                 230                 235                 240 cca tac cag aag gtc ctg gac ggc gtc ctc aac tat ccg atc tac tgg     768
Pro Tyr Gln Lys Val Leu Asp Gly Val Leu Asn Tyr Pro Ile Tyr Trp
                245                 250                 255 caa ctc ctc tac gcc ttc gaa tcc tcc agc ggc agc atc agc aat ctc     816
Gln Leu Leu Tyr Ala Phe Glu Ser Ser Ser Gly Ser Ile Ser Asn Leu
            260                 265                 270 tac aac atg atc aaa tcc gtc gca agc gac tgc tcc gat ccg aca cta    864
Tyr Asn Met Ile Lys Ser Val Ala Ser Asp Cys Ser Asp Pro Thr Leu
        275                 280                 285 ctc ggc aac ttc atc gaa aac cac gac aat ccc cgt ttc gcc tcc tac    912
Leu Gly Asn Phe Ile Glu Asn His Asp Asn Pro Arg Phe Ala Ser Tyr
    290                 295                 300 acc tcc gac tac tcg caa gcc aaa aac gtc ctc agc tac atc ttc ctc    960
Thr Ser Asp Tyr Ser Gln Ala Lys Asn Val Leu Ser Tyr Ile Phe Leu
305                 310                 315                 320 tcc gac ggc atc ccc atc gtc tac gcc ggc gaa gaa cag cac tac tcc   1008
Ser Asp Gly Ile Pro Ile Val Tyr Ala Gly Glu Glu Gln His Tyr Ser
                325                 330                 335 ggc ggc aag gtg ccc tac aac cgc gaa gcg acc tgg ctt tca ggc tac   1056
Gly Gly Lys Val Pro Tyr Asn Arg Glu Ala Thr Trp Leu Ser Gly Tyr
            340                 345                 350 gac acc tcc gca gag ctg tac acc tgg ata gcc acc acg aac gcg atc   1104
Asp Thr Ser Ala Glu Leu Tyr Thr Trp Ile Ala Thr Thr Asn Ala Ile
        355                 360                 365 cgc aaa cta gcc atc tca gct gac tcg gcc tac att acc tac gcg aat   1152
Arg Lys Leu Ala Ile Ser Ala Asp Ser Ala Tyr Ile Thr Tyr Ala Asn
    370                 375                 380 gat gca ttc tac act gac agc aac acc atc gca atg cgc aaa ggc acc   1200
Asp Ala Phe Tyr Thr Asp Ser Asn Thr Ile Ala Met Arg Lys Gly Thr
385                 390                 395                 400 tca ggg agc caa gtc atc acc gtc ctc tcc aac aaa ggc tcc tca gga   1248
Ser Gly Ser Gln Val Ile Thr Val Leu Ser Asn Lys Gly Ser Ser Gly
                405                 410                 415 agc agc tac acc ctg acc ctc agc gga agc ggc tac aca tcc ggc acg   1296
Ser Ser Tyr Thr Leu Thr Leu Ser Gly Ser Gly Tyr Thr Ser Gly Thr
            420                 425                 430 aag ctg atc gaa gcg tac aca tgc aca tcc gtg acc gtg gac tcg agc   1344
Lys Leu Ile Glu Ala Tyr Thr Cys Thr Ser Val Thr Val Asp Ser Ser
        435                 440                 445 ggc gat att ccc gtg ccg atg gcg tcg gga tta ccg aga gtt ctt ctg   1392
Gly Asp Ile Pro Val Pro Met Ala Ser Gly Leu Pro Arg Val Leu Leu
    450                 455                 460 ccc gcg tcc gtc gtc gat agc tct tcg ctc tgt ggc ggg agc gga aga   1440
Pro Ala Ser Val Val Asp Ser Ser Ser Leu Cys Gly Gly Ser Gly Arg
465                 470                 475                 480 aca acc acg acc aca act gct gct gct act agt aca tcc aaa gcc acc   1488
Thr Thr Thr Thr Thr Thr Ala Ala Ala Thr Ser Thr Ser Lys Ala Thr
                485                 490                 495 acc tcc tct tct tct tct gct gct gct act act tct tca tca gtc      1536
Thr Ser Ser Ser Ser Ser Ala Ala Ala Thr Thr Ser Ser Val
            500                 505                 510 gag gtc act ttc gac gtt tac gct acc aca gta tat ggc cag aac atc   1584
Glu Val Thr Phe Asp Val Tyr Ala Thr Thr Val Tyr Gly Gln Asn Ile
```

```
                       515                 520                 525
tat atc acc ggt gat gtg agt gag ctc ggc aac tgg aca ccc gcc aat    1632
Tyr Ile Thr Gly Asp Val Ser Glu Leu Gly Asn Trp Thr Pro Ala Asn
        530                 535                 540 ggt gtt gca ctc tct tct gct aac tac ccc acc tgg agt gcc acg atc    1680
Gly Val Ala Leu Ser Ser Ala Asn Tyr Pro Thr Trp Ser Ala Thr Ile
545                 550                 555                 560 gct ctc ccc gct gac acg aca atc cag tac aag tat gtc aac att gac    1728
Ala Leu Pro Ala Asp Thr Thr Ile Gln Tyr Lys Tyr Val Asn Ile Asp
                565                 570                 575 ggc agc acc gtc atc tgg gag gat gct atc agc aat cgc gag atc acg    1776
Gly Ser Thr Val Ile Trp Glu Asp Ala Ile Ser Asn Arg Glu Ile Thr
        580                 585                 590 acg ccc gcc agc ggc aca tac acc gaa aaa gac act tgg gat gaa tct    1824
Thr Pro Ala Ser Gly Thr Tyr Thr Glu Lys Asp Thr Trp Asp Glu Ser
                595                 600                 605 tag                                                                1827

<210> SEQ ID NO 35
<211> LENGTH: 608
<212> TYPE: PRT
<213> ORGANISM: Artificial sequence
<220> FEATURE:
<223> OTHER INFORMATION: Synthetic Construct

<400> SEQUENCE: 35

Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asp Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
    50                  55                  60

Ile Thr Glu Gln Leu Pro Gln Asp Thr Ala Asp Gly Glu Ala Tyr His
65              70                  75                  80

Gly Tyr Trp Gln Gln Lys Ile Tyr Asp Val Asn Ser Asn Phe Gly Thr
            85                  90                  95

Ala Asp Asp Leu Lys Ser Leu Ser Asp Ala Leu His Ala Arg Gly Met
        100                 105                 110

Tyr Leu Met Val Asp Val Val Pro Asn His Met Gly Tyr Ala Gly Asn
    115                 120                 125

Gly Asn Asp Val Asp Tyr Ser Val Phe Asp Pro Phe Asp Ser Ser Ser
130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
            165                 170                 175

Asn Thr Thr Glu Thr Ala Val Arg Thr Ile Trp Tyr Asp Trp Val Ala
        180                 185                 190

Asp Leu Val Ser Asn Tyr Ser Val Asp Gly Leu Arg Ile Asp Ser Val
    195                 200                 205

Leu Glu Val Glu Pro Asp Phe Phe Pro Gly Tyr Gln Glu Ala Ala Gly
    210                 215                 220

Val Tyr Cys Val Gly Glu Val Asp Asn Gly Asn Pro Ala Leu Asp Cys
225                 230                 235                 240

Pro Tyr Gln Lys Val Leu Asp Gly Val Leu Asn Tyr Pro Ile Tyr Trp
```

```
                    245                 250                 255
Gln Leu Leu Tyr Ala Phe Glu Ser Ser Ser Gly Ser Ile Ser Asn Leu
            260                 265                 270

Tyr Asn Met Ile Lys Ser Val Ala Ser Asp Cys Ser Asp Pro Thr Leu
        275                 280                 285

Leu Gly Asn Phe Ile Glu Asn His Asp Asn Pro Arg Phe Ala Ser Tyr
    290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Gln His Tyr Ser
                325                 330                 335

Gly Gly Lys Val Pro Tyr Asn Arg Glu Ala Thr Trp Leu Ser Gly Tyr
                340                 345                 350

Asp Thr Ser Ala Glu Leu Tyr Thr Trp Ile Ala Thr Asn Ala Ile
                355                 360                 365

Arg Lys Leu Ala Ile Ser Ala Asp Ser Ala Tyr Ile Thr Tyr Ala Asn
    370                 375                 380

Asp Ala Phe Tyr Thr Asp Ser Asn Thr Ile Ala Met Arg Lys Gly Thr
385                 390                 395                 400

Ser Gly Ser Gln Val Ile Thr Val Leu Ser Asn Lys Gly Ser Ser Gly
                405                 410                 415

Ser Ser Tyr Thr Leu Thr Leu Ser Gly Ser Gly Tyr Thr Ser Gly Thr
                420                 425                 430

Lys Leu Ile Glu Ala Tyr Thr Cys Thr Ser Val Thr Val Asp Ser Ser
            435                 440                 445

Gly Asp Ile Pro Val Pro Met Ala Ser Gly Leu Pro Arg Val Leu Leu
    450                 455                 460

Pro Ala Ser Val Val Asp Ser Ser Ser Leu Cys Gly Gly Ser Gly Arg
465                 470                 475                 480

Thr Thr Thr Thr Thr Ala Ala Ala Thr Ser Thr Ser Lys Ala Thr
                485                 490                 495

Thr Ser Ser Ser Ser Ser Ala Ala Ala Thr Thr Ser Ser Ser Val
            500                 505                 510

Glu Val Thr Phe Asp Val Tyr Ala Thr Thr Val Tyr Gly Gln Asn Ile
            515                 520                 525

Tyr Ile Thr Gly Asp Val Ser Glu Leu Gly Asn Trp Thr Pro Ala Asn
    530                 535                 540

Gly Val Ala Leu Ser Ser Ala Asn Tyr Pro Thr Trp Ser Ala Thr Ile
545                 550                 555                 560

Ala Leu Pro Ala Asp Thr Thr Ile Gln Tyr Lys Tyr Val Asn Ile Asp
                565                 570                 575

Gly Ser Thr Val Ile Trp Glu Asp Ala Ile Ser Asn Arg Glu Ile Thr
            580                 585                 590

Thr Pro Ala Ser Gly Thr Tyr Thr Glu Lys Asp Thr Trp Asp Glu Ser
    595                 600                 605

<210> SEQ ID NO 36
<211> LENGTH: 1863
<212> TYPE: DNA
<213> ORGANISM: Artificial
<220> FEATURE:
<223> OTHER INFORMATION: Hybrid consisting of A.oryzae alpha-amylase
      catalytic domain-A. kawachii alpha-amylase linker-A. kawachi
      alpha-amylase CBD
<220> FEATURE:
<221> NAME/KEY: CDS
<222> LOCATION: (1)..(1863)
```

<223> OTHER INFORMATION: Hybrid

<400> SEQUENCE: 36

| | | | | | | | | | | | | | | | | |
|---|---|---|---|---|---|---|---|---|---|---|---|---|---|---|---|---|
| gca | acg | cct | gcg | gac | tgg | cga | tcg | caa | tcc | att | tat | ttc | ctt | ctc | acg | 48 |
| Ala | Thr | Pro | Ala | Asp | Trp | Arg | Ser | Gln | Ser | Ile | Tyr | Phe | Leu | Leu | Thr | |
| 1 | | | 5 | | | | | 10 | | | | | 15 | | | |

| gat | cga | ttt | gca | agg | acg | gat | ggg | tcg | acg | act | gcg | act | tgt | aat | act | 96 |
|---|---|---|---|---|---|---|---|---|---|---|---|---|---|---|---|---|
| Asp | Arg | Phe | Ala | Arg | Thr | Asp | Gly | Ser | Thr | Thr | Ala | Thr | Cys | Asn | Thr | |
| | | | 20 | | | | | 25 | | | | | 30 | | | |

| gcg | gat | cag | aaa | tac | tgt | ggt | gga | aca | tgg | cag | ggc | atc | atc | gac | aag | 144 |
|---|---|---|---|---|---|---|---|---|---|---|---|---|---|---|---|---|
| Ala | Asp | Gln | Lys | Tyr | Cys | Gly | Gly | Thr | Trp | Gln | Gly | Ile | Ile | Asp | Lys | |
| | | 35 | | | | | 40 | | | | | 45 | | | | |

| ttg | gac | tat | atc | cag | gga | atg | ggc | ttc | aca | gcc | atc | tgg | atc | acc | ccc | 192 |
|---|---|---|---|---|---|---|---|---|---|---|---|---|---|---|---|---|
| Leu | Asp | Tyr | Ile | Gln | Gly | Met | Gly | Phe | Thr | Ala | Ile | Trp | Ile | Thr | Pro | |
| 50 | | | | | 55 | | | | | 60 | | | | | | |

| gtt | aca | gcc | cag | ctg | ccc | cag | acc | acc | gca | tat | gga | gat | gcc | tac | cat | 240 |
|---|---|---|---|---|---|---|---|---|---|---|---|---|---|---|---|---|
| Val | Thr | Ala | Gln | Leu | Pro | Gln | Thr | Thr | Ala | Tyr | Gly | Asp | Ala | Tyr | His | |
| 65 | | | | | 70 | | | | | 75 | | | | | 80 | |

| ggc | tac | tgg | cag | cag | gat | ata | tac | tct | ctg | aac | gaa | aac | tac | ggc | act | 288 |
|---|---|---|---|---|---|---|---|---|---|---|---|---|---|---|---|---|
| Gly | Tyr | Trp | Gln | Gln | Asp | Ile | Tyr | Ser | Leu | Asn | Glu | Asn | Tyr | Gly | Thr | |
| | | | | 85 | | | | | 90 | | | | | 95 | | |

| gca | gat | gac | ttg | aag | gcg | ctc | tct | tcg | gcc | ctt | cat | gag | agg | ggg | atg | 336 |
|---|---|---|---|---|---|---|---|---|---|---|---|---|---|---|---|---|
| Ala | Asp | Asp | Leu | Lys | Ala | Leu | Ser | Ser | Ala | Leu | His | Glu | Arg | Gly | Met | |
| | | | 100 | | | | | 105 | | | | | 110 | | | |

| tat | ctt | atg | gtc | gat | gtg | gtt | gct | aac | cat | atg | ggc | tat | gat | gga | gcg | 384 |
|---|---|---|---|---|---|---|---|---|---|---|---|---|---|---|---|---|
| Tyr | Leu | Met | Val | Asp | Val | Val | Ala | Asn | His | Met | Gly | Tyr | Asp | Gly | Ala | |
| | | 115 | | | | | 120 | | | | | 125 | | | | |

| ggt | agc | tca | gtc | gat | tac | agt | gtg | ttt | aaa | ccg | ttc | agt | tcc | caa | gac | 432 |
|---|---|---|---|---|---|---|---|---|---|---|---|---|---|---|---|---|
| Gly | Ser | Ser | Val | Asp | Tyr | Ser | Val | Phe | Lys | Pro | Phe | Ser | Ser | Gln | Asp | |
| 130 | | | | | 135 | | | | | 140 | | | | | | |

| tac | ttc | cac | ccg | ttc | tgt | ttc | att | caa | aac | tat | gaa | gat | cag | act | cag | 480 |
|---|---|---|---|---|---|---|---|---|---|---|---|---|---|---|---|---|
| Tyr | Phe | His | Pro | Phe | Cys | Phe | Ile | Gln | Asn | Tyr | Glu | Asp | Gln | Thr | Gln | |
| 145 | | | | | 150 | | | | | 155 | | | | | 160 | |

| gtt | gag | gat | tgc | tgg | cta | gga | gat | aac | act | gtc | tcc | ttg | cct | gat | ctc | 528 |
|---|---|---|---|---|---|---|---|---|---|---|---|---|---|---|---|---|
| Val | Glu | Asp | Cys | Trp | Leu | Gly | Asp | Asn | Thr | Val | Ser | Leu | Pro | Asp | Leu | |
| | | | | 165 | | | | | 170 | | | | | 175 | | |

| gat | acc | acc | aag | gat | gtg | gtc | aag | aat | gaa | tgg | tac | gac | tgg | gtg | gga | 576 |
|---|---|---|---|---|---|---|---|---|---|---|---|---|---|---|---|---|
| Asp | Thr | Thr | Lys | Asp | Val | Val | Lys | Asn | Glu | Trp | Tyr | Asp | Trp | Val | Gly | |
| | | | 180 | | | | | 185 | | | | | 190 | | | |

| tca | ttg | gta | tcg | aac | tac | tcc | att | gac | ggc | ctc | cgt | atc | gac | aca | gta | 624 |
|---|---|---|---|---|---|---|---|---|---|---|---|---|---|---|---|---|
| Ser | Leu | Val | Ser | Asn | Tyr | Ser | Ile | Asp | Gly | Leu | Arg | Ile | Asp | Thr | Val | |
| | | 195 | | | | | 200 | | | | | 205 | | | | |

| aaa | cac | gtc | cag | aag | gac | ttc | tgg | ccc | ggg | tac | aac | aaa | gcc | gca | ggc | 672 |
|---|---|---|---|---|---|---|---|---|---|---|---|---|---|---|---|---|
| Lys | His | Val | Gln | Lys | Asp | Phe | Trp | Pro | Gly | Tyr | Asn | Lys | Ala | Ala | Gly | |
| | | 210 | | | | | 215 | | | | | 220 | | | | |

| gtg | tac | tgt | atc | ggc | gag | gtg | ctc | gac | ggt | gat | ccg | gcc | tac | act | tgt | 720 |
|---|---|---|---|---|---|---|---|---|---|---|---|---|---|---|---|---|
| Val | Tyr | Cys | Ile | Gly | Glu | Val | Leu | Asp | Gly | Asp | Pro | Ala | Tyr | Thr | Cys | |
| 225 | | | | | 230 | | | | | 235 | | | | | 240 | |

| ccc | tac | cag | aac | gtc | atg | gac | ggc | gta | ctg | aac | tat | ccc | att | tac | tat | 768 |
|---|---|---|---|---|---|---|---|---|---|---|---|---|---|---|---|---|
| Pro | Tyr | Gln | Asn | Val | Met | Asp | Gly | Val | Leu | Asn | Tyr | Pro | Ile | Tyr | Tyr | |
| | | | | 245 | | | | | 250 | | | | | 255 | | |

| cca | ctc | ctc | aac | gcc | ttc | aag | tca | acc | tcc | ggc | agc | atg | gac | gac | ctc | 816 |
|---|---|---|---|---|---|---|---|---|---|---|---|---|---|---|---|---|
| Pro | Leu | Leu | Asn | Ala | Phe | Lys | Ser | Thr | Ser | Gly | Ser | Met | Asp | Asp | Leu | |
| | | | 260 | | | | | 265 | | | | | 270 | | | |

| tac | aac | atg | atc | aac | acc | gtc | aaa | tcc | gac | tgt | cca | gac | tca | aca | ctc | 864 |
|---|---|---|---|---|---|---|---|---|---|---|---|---|---|---|---|---|
| Tyr | Asn | Met | Ile | Asn | Thr | Val | Lys | Ser | Asp | Cys | Pro | Asp | Ser | Thr | Leu | |
| | | 275 | | | | | 280 | | | | | 285 | | | | |

| ctg | ggc | aca | ttc | gtc | gag | aac | cac | gac | aac | cca | cgg | ttc | gct | tct | tac | 912 |
|---|---|---|---|---|---|---|---|---|---|---|---|---|---|---|---|---|
| Leu | Gly | Thr | Phe | Val | Glu | Asn | His | Asp | Asn | Pro | Arg | Phe | Ala | Ser | Tyr | |
| | | 290 | | | | | 295 | | | | | 300 | | | | |

```
acc aac gac ata gcc ctc gcc aag aac gtc gca gca ttc atc atc ctc    960
Thr Asn Asp Ile Ala Leu Ala Lys Asn Val Ala Ala Phe Ile Ile Leu
305             310                 315                 320 aac gac gga atc ccc atc atc tac gcc ggc caa gaa cag cac tac gcc   1008
Asn Asp Gly Ile Pro Ile Ile Tyr Ala Gly Gln Glu Gln His Tyr Ala
            325                 330                 335 ggc gga aac gac ccc gcg aac cgc gaa gca acc tgg ctc tcg ggc tac   1056
Gly Gly Asn Asp Pro Ala Asn Arg Glu Ala Thr Trp Leu Ser Gly Tyr
        340                 345                 350 ccg acc gac agc gag ctg tac aag tta att gcc tcc gcg aac gca atc   1104
Pro Thr Asp Ser Glu Leu Tyr Lys Leu Ile Ala Ser Ala Asn Ala Ile
    355                 360                 365 cgg aac tat gcc att agc aaa gat aca gga ttc gtg acc tac aag aac   1152
Arg Asn Tyr Ala Ile Ser Lys Asp Thr Gly Phe Val Thr Tyr Lys Asn
370                 375                 380 tgg ccc atc tac aaa gac gac aca acg atc gcc atg cgc aag ggc aca   1200
Trp Pro Ile Tyr Lys Asp Asp Thr Thr Ile Ala Met Arg Lys Gly Thr
385                 390                 395                 400 gat ggg tcg cag atc gtg act atc ttg tcc aac aag ggt gct tcg ggt   1248
Asp Gly Ser Gln Ile Val Thr Ile Leu Ser Asn Lys Gly Ala Ser Gly
            405                 410                 415 gat tcg tat acc ctc tcc ttg agt ggt gcg ggt tac aca gcc ggc cag   1296
Asp Ser Tyr Thr Leu Ser Leu Ser Gly Ala Gly Tyr Thr Ala Gly Gln
        420                 425                 430 caa ttg acg gag gtc att ggc tgc acg acc gtg acg gtt ggt tcg gat   1344
Gln Leu Thr Glu Val Ile Gly Cys Thr Thr Val Thr Val Gly Ser Asp
    435                 440                 445 gga aat gtg cct gtt cct atg gca ggt ggg cta cct agg gta ttg tat   1392
Gly Asn Val Pro Val Pro Met Ala Gly Gly Leu Pro Arg Val Leu Tyr
450                 455                 460 ccg act gag aag ttg gca ggt agc aag atc tgt agt agc tcg gga aga   1440
Pro Thr Glu Lys Leu Ala Gly Ser Lys Ile Cys Ser Ser Ser Gly Arg
465                 470                 475                 480 aca acc acg acc aca act gct gct gct act agt aca tcc aaa gcc acc   1488
Thr Thr Thr Thr Thr Thr Ala Ala Ala Thr Ser Thr Ser Lys Ala Thr
            485                 490                 495 acc tcc tct tct tct tct tct gct gct gct act act tct tca tca tgc   1536
Thr Ser Ser Ser Ser Ser Ser Ala Ala Ala Thr Thr Ser Ser Ser Cys
        500                 505                 510 acc gca aca agc acc acc ctc ccc atc acc ttc gaa gaa ctc gtc acc   1584
Thr Ala Thr Ser Thr Thr Leu Pro Ile Thr Phe Glu Glu Leu Val Thr
    515                 520                 525 act acc tac ggg gaa gaa gtc tac ctc agc gga tct atc tcc cag ctc   1632
Thr Thr Tyr Gly Glu Glu Val Tyr Leu Ser Gly Ser Ile Ser Gln Leu
530                 535                 540 gga gag tgg gat acg agt gac gcg gtg aag ttg tcc gcg gat gat tat   1680
Gly Glu Trp Asp Thr Ser Asp Ala Val Lys Leu Ser Ala Asp Asp Tyr
545                 550                 555                 560 acc tcg agt aac ccc gag tgg tct gtt act gtg tcg ttg ccg gtg ggg   1728
Thr Ser Ser Asn Pro Glu Trp Ser Val Thr Val Ser Leu Pro Val Gly
            565                 570                 575 acg acc ttc gag tat aag ttt att aag gtc gat gag ggt gga agt gtg   1776
Thr Thr Phe Glu Tyr Lys Phe Ile Lys Val Asp Glu Gly Gly Ser Val
        580                 585                 590 act tgg gaa agt gat ccg aat agg gag tat act gtg cct gaa tgt ggg   1824
Thr Trp Glu Ser Asp Pro Asn Arg Glu Tyr Thr Val Pro Glu Cys Gly
    595                 600                 605 aat ggg agt ggg gag acg gtg gtt gat acg tgg agg tag               1863
Asn Gly Ser Gly Glu Thr Val Val Asp Thr Trp Arg
610                 615                 620
```

<210> SEQ ID NO 37
<211> LENGTH: 620
<212> TYPE: PRT
<213> ORGANISM: Artificial
<220> FEATURE:
<223> OTHER INFORMATION: Synthetic Construct

<400> SEQUENCE: 37

```
Ala Thr Pro Ala Asp Trp Arg Ser Gln Ser Ile Tyr Phe Leu Leu Thr
 1               5                  10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ser Ala Leu His Glu Arg Gly Met
            100                 105                 110

Tyr Leu Met Val Asp Val Val Ala Asn His Met Gly Tyr Asp Gly Ala
        115                 120                 125

Gly Ser Ser Val Asp Tyr Ser Val Phe Lys Pro Phe Ser Ser Gln Asp
    130                 135                 140

Tyr Phe His Pro Phe Cys Phe Ile Gln Asn Tyr Glu Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
    210                 215                 220

Val Tyr Cys Ile Gly Glu Val Leu Asp Gly Asp Pro Ala Tyr Thr Cys
225                 230                 235                 240

Pro Tyr Gln Asn Val Met Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270

Tyr Asn Met Ile Asn Thr Val Lys Ser Asp Cys Pro Asp Ser Thr Leu
        275                 280                 285

Leu Gly Thr Phe Val Glu Asn His Asp Asn Pro Arg Phe Ala Ser Tyr
    290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
                325                 330                 335

Gly Gly Asn Asp Pro Ala Asn Arg Glu Ala Thr Trp Leu Ser Gly Tyr
            340                 345                 350

Pro Thr Asp Ser Glu Leu Tyr Lys Leu Ile Ala Ser Ala Asn Ala Ile
        355                 360                 365

Arg Asn Tyr Ala Ile Ser Lys Asp Thr Gly Phe Val Thr Tyr Lys Asn
```

```
                  370                 375                 380
Trp Pro Ile Tyr Lys Asp Asp Thr Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
            420                 425                 430

Gln Leu Thr Glu Val Ile Gly Cys Thr Thr Val Thr Val Gly Ser Asp
        435                 440                 445

Gly Asn Val Pro Val Pro Met Ala Gly Gly Leu Pro Arg Val Leu Tyr
450                 455                 460

Pro Thr Glu Lys Leu Ala Gly Ser Lys Ile Cys Ser Ser Gly Arg
465                 470                 475                 480

Thr Thr Thr Thr Thr Thr Ala Ala Ala Thr Ser Ser Lys Ala Thr
                485                 490                 495

Thr Ser Ser Ser Ser Ser Ser Ala Ala Ala Thr Thr Ser Ser Ser Cys
            500                 505                 510

Thr Ala Thr Ser Thr Thr Leu Pro Ile Thr Phe Glu Glu Leu Val Thr
        515                 520                 525

Thr Thr Tyr Gly Glu Glu Val Tyr Leu Ser Gly Ser Ile Ser Gln Leu
    530                 535                 540

Gly Glu Trp Asp Thr Ser Asp Ala Val Lys Leu Ser Ala Asp Asp Tyr
545                 550                 555                 560

Thr Ser Ser Asn Pro Glu Trp Ser Val Thr Val Ser Leu Pro Val Gly
                565                 570                 575

Thr Thr Phe Glu Tyr Lys Phe Ile Lys Val Asp Glu Gly Gly Ser Val
            580                 585                 590

Thr Trp Glu Ser Asp Pro Asn Arg Glu Tyr Thr Val Pro Glu Cys Gly
        595                 600                 605

Asn Gly Ser Gly Glu Thr Val Val Asp Thr Trp Arg
    610                 615                 620

<210> SEQ ID NO 38
<211> LENGTH: 1767
<212> TYPE: DNA
<213> ORGANISM: Artificial sequence
<220> FEATURE:
<223> OTHER INFORMATION: Hybrid consisting of A. niger acid
      alpha-amylase catalytic domain- A.rolfsii glucoamylase linker- A.
      rolfsii glucoamylase CBM
<220> FEATURE:
<221> NAME/KEY: CDS
<222> LOCATION: (1)..(1767)
<223> OTHER INFORMATION: Hybrid

<400> SEQUENCE: 38 ctg tcg gct gca gaa tgg cgc act cag tcg att tac ttc cta ttg acg      48
Leu Ser Ala Ala Glu Trp Arg Thr Gln Ser Ile Tyr Phe Leu Leu Thr
1               5                   10                  15 gat cgg ttc ggt agg acg gac aat tcg acg aca gct aca tgc gat acg      96
Asp Arg Phe Gly Arg Thr Asp Asn Ser Thr Thr Ala Thr Cys Asp Thr
            20                  25                  30 ggt gac caa atc tat tgt ggt ggc agt tgg caa gga atc atc aac cat     144
Gly Asp Gln Ile Tyr Cys Gly Gly Ser Trp Gln Gly Ile Ile Asn His
        35                  40                  45 ctg gat tat atc cag ggc atg gga ttc acg gcc atc tgg atc tcg cct     192
Leu Asp Tyr Ile Gln Gly Met Gly Phe Thr Ala Ile Trp Ile Ser Pro
    50                  55                  60 atc act gaa cag ctg ccc cag gat act gct gat ggt gaa gct tac cat     240
```

| | | | | | | | | | | | | | | | |
|---|---|---|---|---|---|---|---|---|---|---|---|---|---|---|---|
| Ile | Thr | Glu | Gln | Leu | Pro | Gln | Asp | Thr | Ala | Asp | Gly | Glu | Ala | Tyr | His |
| 65 | | | | 70 | | | | | 75 | | | | | | 80 |

| | | | | | | | | | | | | | | | |
|---|---|---|---|---|---|---|---|---|---|---|---|---|---|---|---|
| gga | tat | tgg | cag | cag | aag | ata | tac | gac | gtg | aac | tcc | aac | ttc | ggc | act | 288 |
| Gly | Tyr | Trp | Gln | Gln | Lys | Ile | Tyr | Asp | Val | Asn | Ser | Asn | Phe | Gly | Thr |
| | | | | 85 | | | | | 90 | | | | | 95 | |

| gca | gat | gac | ctc | aag | tcc | ctc | tca | gat | gcg | ctt | cat | gcc | cgc | gga | atg | 336 |
|---|---|---|---|---|---|---|---|---|---|---|---|---|---|---|---|---|
| Ala | Asp | Asp | Leu | Lys | Ser | Leu | Ser | Asp | Ala | Leu | His | Ala | Arg | Gly | Met |
| | | | | 100 | | | | | 105 | | | | | 110 | |

| tac | ctc | atg | gtg | gac | gtc | gtc | cct | aac | cac | atg | ggc | tac | gcc | ggc | aac | 384 |
|---|---|---|---|---|---|---|---|---|---|---|---|---|---|---|---|---|
| Tyr | Leu | Met | Val | Asp | Val | Val | Pro | Asn | His | Met | Gly | Tyr | Ala | Gly | Asn |
| | | | 115 | | | | | 120 | | | | | 125 | | |

| ggc | aac | gat | gta | gac | tac | agc | gtc | ttc | gac | ccc | ttc | gat | tcc | tcc | tcc | 432 |
|---|---|---|---|---|---|---|---|---|---|---|---|---|---|---|---|---|
| Gly | Asn | Asp | Val | Asp | Tyr | Ser | Val | Phe | Asp | Pro | Phe | Asp | Ser | Ser | Ser |
| | 130 | | | | | 135 | | | | | 140 | | | | |

| tac | ttc | cac | cca | tac | tgc | ctg | atc | aca | gat | tgg | gac | aac | ttg | acc | atg | 480 |
|---|---|---|---|---|---|---|---|---|---|---|---|---|---|---|---|---|
| Tyr | Phe | His | Pro | Tyr | Cys | Leu | Ile | Thr | Asp | Trp | Asp | Asn | Leu | Thr | Met |
| 145 | | | | | 150 | | | | | 155 | | | | | 160 |

| gtc | caa | gat | tgt | tgg | gag | ggt | gac | acc | atc | gta | tct | ctg | cca | gac | cta | 528 |
|---|---|---|---|---|---|---|---|---|---|---|---|---|---|---|---|---|
| Val | Gln | Asp | Cys | Trp | Glu | Gly | Asp | Thr | Ile | Val | Ser | Leu | Pro | Asp | Leu |
| | | | | 165 | | | | | 170 | | | | | 175 | |

| aac | acc | acc | gaa | act | gcc | gtg | aga | aca | atc | tgg | tat | gac | tgg | gta | gcc | 576 |
|---|---|---|---|---|---|---|---|---|---|---|---|---|---|---|---|---|
| Asn | Thr | Thr | Glu | Thr | Ala | Val | Arg | Thr | Ile | Trp | Tyr | Asp | Trp | Val | Ala |
| | | | | 180 | | | | | 185 | | | | | 190 | |

| gac | ctg | gta | tcc | aat | tat | tca | gtc | gac | gga | ctc | cgc | atc | gac | agt | gtc | 624 |
|---|---|---|---|---|---|---|---|---|---|---|---|---|---|---|---|---|
| Asp | Leu | Val | Ser | Asn | Tyr | Ser | Val | Asp | Gly | Leu | Arg | Ile | Asp | Ser | Val |
| | | | 195 | | | | | 200 | | | | | 205 | | |

| ctc | gaa | gtc | gaa | cca | gac | ttc | ttc | ccg | ggc | tac | cag | gaa | gca | gca | ggt | 672 |
|---|---|---|---|---|---|---|---|---|---|---|---|---|---|---|---|---|
| Leu | Glu | Val | Glu | Pro | Asp | Phe | Phe | Pro | Gly | Tyr | Gln | Glu | Ala | Ala | Gly |
| | 210 | | | | | 215 | | | | | 220 | | | | |

| gtc | tac | tgc | gtc | ggc | gaa | gtc | gac | aac | ggc | aac | cct | gcc | ctc | gac | tgc | 720 |
|---|---|---|---|---|---|---|---|---|---|---|---|---|---|---|---|---|
| Val | Tyr | Cys | Val | Gly | Glu | Val | Asp | Asn | Gly | Asn | Pro | Ala | Leu | Asp | Cys |
| 225 | | | | | 230 | | | | | 235 | | | | | 240 |

| cca | tac | cag | aag | gtc | ctg | gac | ggc | gtc | ctc | aac | tat | ccg | atc | tac | tgg | 768 |
|---|---|---|---|---|---|---|---|---|---|---|---|---|---|---|---|---|
| Pro | Tyr | Gln | Lys | Val | Leu | Asp | Gly | Val | Leu | Asn | Tyr | Pro | Ile | Tyr | Trp |
| | | | | 245 | | | | | 250 | | | | | 255 | |

| caa | ctc | ctc | tac | gcc | ttc | gaa | tcc | tcc | agc | ggc | agc | atc | agc | aat | ctc | 816 |
|---|---|---|---|---|---|---|---|---|---|---|---|---|---|---|---|---|
| Gln | Leu | Leu | Tyr | Ala | Phe | Glu | Ser | Ser | Ser | Gly | Ser | Ile | Ser | Asn | Leu |
| | | | 260 | | | | | 265 | | | | | 270 | | |

| tac | aac | atg | atc | aaa | tcc | gtc | gca | agc | gac | tgc | tcc | gat | ccg | aca | cta | 864 |
|---|---|---|---|---|---|---|---|---|---|---|---|---|---|---|---|---|
| Tyr | Asn | Met | Ile | Lys | Ser | Val | Ala | Ser | Asp | Cys | Ser | Asp | Pro | Thr | Leu |
| | | 275 | | | | | 280 | | | | | 285 | | | |

| ctc | ggc | aac | ttc | atc | gaa | aac | cac | gac | aat | ccc | cgt | ttc | gcc | tcc | tac | 912 |
|---|---|---|---|---|---|---|---|---|---|---|---|---|---|---|---|---|
| Leu | Gly | Asn | Phe | Ile | Glu | Asn | His | Asp | Asn | Pro | Arg | Phe | Ala | Ser | Tyr |
| | 290 | | | | | 295 | | | | | 300 | | | | |

| acc | tcc | gac | tac | tcg | caa | gcc | aaa | aac | gtc | ctc | agc | tac | atc | ttc | ctc | 960 |
|---|---|---|---|---|---|---|---|---|---|---|---|---|---|---|---|---|
| Thr | Ser | Asp | Tyr | Ser | Gln | Ala | Lys | Asn | Val | Leu | Ser | Tyr | Ile | Phe | Leu |
| 305 | | | | | 310 | | | | | 315 | | | | | 320 |

| tcc | gac | ggc | atc | ccc | atc | gtc | tac | gcc | ggc | gaa | gaa | cag | cac | tac | tcc | 1008 |
|---|---|---|---|---|---|---|---|---|---|---|---|---|---|---|---|---|
| Ser | Asp | Gly | Ile | Pro | Ile | Val | Tyr | Ala | Gly | Glu | Glu | Gln | His | Tyr | Ser |
| | | | | 325 | | | | | 330 | | | | | 335 | |

| ggc | ggc | aag | gtg | ccc | tac | aac | cgc | gaa | gcg | acc | tgg | ctt | tca | ggc | tac | 1056 |
|---|---|---|---|---|---|---|---|---|---|---|---|---|---|---|---|---|
| Gly | Gly | Lys | Val | Pro | Tyr | Asn | Arg | Glu | Ala | Thr | Trp | Leu | Ser | Gly | Tyr |
| | | | 340 | | | | | 345 | | | | | 350 | | |

| gac | acc | tcc | gca | gag | ctg | tac | acc | tgg | ata | gcc | acc | acg | aac | gcg | atc | 1104 |
|---|---|---|---|---|---|---|---|---|---|---|---|---|---|---|---|---|
| Asp | Thr | Ser | Ala | Glu | Leu | Tyr | Thr | Trp | Ile | Ala | Thr | Thr | Asn | Ala | Ile |
| | | 355 | | | | | 360 | | | | | 365 | | | |

| cgc | aaa | cta | gcc | atc | tca | gct | gac | tcg | gcc | tac | att | acc | tac | gcg | aat | 1152 |
|---|---|---|---|---|---|---|---|---|---|---|---|---|---|---|---|---|
| Arg | Lys | Leu | Ala | Ile | Ser | Ala | Asp | Ser | Ala | Tyr | Ile | Thr | Tyr | Ala | Asn |
| | 370 | | | | | 375 | | | | | 380 | | | | |

| gat | gca | ttc | tac | act | gac | agc | aac | acc | atc | gca | atg | cgc | aaa | ggc | acc | 1200 |

```
Asp Ala Phe Tyr Thr Asp Ser Asn Thr Ile Ala Met Arg Lys Gly Thr
385                 390                 395                 400 tca ggg agc caa gtc atc acc gtc ctc tcc aac aaa ggc tcc tca gga       1248
Ser Gly Ser Gln Val Ile Thr Val Leu Ser Asn Lys Gly Ser Ser Gly
                405                 410                 415 agc agc tac acc ctg acc ctc agc gga agc ggc tac aca tcc ggc acg       1296
Ser Ser Tyr Thr Leu Thr Leu Ser Gly Ser Gly Tyr Thr Ser Gly Thr
            420                 425                 430 aag ctg atc gaa gcg tac aca tgc aca tcc gtg acc gtg gac tcg agc       1344
Lys Leu Ile Glu Ala Tyr Thr Cys Thr Ser Val Thr Val Asp Ser Ser
        435                 440                 445 ggc gat att ccc gtg ccg atg gcg tcg gga tta ccg aga gtt ctt ctg       1392
Gly Asp Ile Pro Val Pro Met Ala Ser Gly Leu Pro Arg Val Leu Leu
    450                 455                 460 ccc gcg tcc gtc gtc gat agc tct tcg ctc tgt ggc ggg agc gga aga       1440
Pro Ala Ser Val Val Asp Ser Ser Ser Leu Cys Gly Gly Ser Gly Arg
465                 470                 475                 480 ggt gct aca agc ccg ggt ggc tcg tcg ggt agt gtc gag gtc act ttc       1488
Gly Ala Thr Ser Pro Gly Gly Ser Ser Gly Ser Val Glu Val Thr Phe
                485                 490                 495 gac gtt tac gct acc aca gta tat ggc cag aac atc tat atc acc ggt       1536
Asp Val Tyr Ala Thr Thr Val Tyr Gly Gln Asn Ile Tyr Ile Thr Gly
            500                 505                 510 gat gtg agt gag ctc ggc aac tgg aca ccc gcc aat ggt gtt gca ctc       1584
Asp Val Ser Glu Leu Gly Asn Trp Thr Pro Ala Asn Gly Val Ala Leu
        515                 520                 525 tct tct gct aac tac ccc acc tgg agt gcc acg atc gct ctc ccc gct       1632
Ser Ser Ala Asn Tyr Pro Thr Trp Ser Ala Thr Ile Ala Leu Pro Ala
    530                 535                 540 gac acg aca atc cag tac aag tat gtc aac att gac ggc agc acc gtc       1680
Asp Thr Thr Ile Gln Tyr Lys Tyr Val Asn Ile Asp Gly Ser Thr Val
545                 550                 555                 560 atc tgg gag gat gct atc agc aat cgc gag atc acg acg ccc gcc agc       1728
Ile Trp Glu Asp Ala Ile Ser Asn Arg Glu Ile Thr Thr Pro Ala Ser
                565                 570                 575 ggc aca tac acc gaa aaa gac act tgg gat gaa tct tag                   1767
Gly Thr Tyr Thr Glu Lys Asp Thr Trp Asp Glu Ser
            580                 585

<210> SEQ ID NO 39
<211> LENGTH: 588
<212> TYPE: PRT
<213> ORGANISM: Artificial sequence
<220> FEATURE:
<223> OTHER INFORMATION: Synthetic Construct

<400> SEQUENCE: 39

Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asp Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
    50                  55                  60

Ile Thr Glu Gln Leu Pro Gln Asp Thr Ala Asp Gly Glu Ala Tyr His
65                  70                  75                  80

Gly Tyr Trp Gln Gln Lys Ile Tyr Asp Val Asn Ser Asn Phe Gly Thr
                85                  90                  95

Ala Asp Asp Leu Lys Ser Leu Ser Asp Ala Leu His Ala Arg Gly Met
```

```
                100             105                 110
Tyr Leu Met Val Asp Val Pro Asn His Met Gly Tyr Ala Gly Asn
            115             120             125

Gly Asn Asp Val Asp Tyr Ser Val Phe Asp Pro Phe Asp Ser Ser
        130              135             140

Tyr Phe His Pro Tyr Cys Leu Ile Thr Asp Trp Asp Asn Leu Thr Met
145             150              155             160

Val Gln Asp Cys Trp Glu Gly Asp Thr Ile Val Ser Leu Pro Asp Leu
                165              170             175

Asn Thr Thr Glu Thr Ala Val Arg Thr Ile Trp Tyr Asp Trp Val Ala
            180              185             190

Asp Leu Val Ser Asn Tyr Ser Val Asp Gly Leu Arg Ile Asp Ser Val
            195             200             205

Leu Glu Val Glu Pro Asp Phe Phe Pro Gly Tyr Gln Glu Ala Ala Gly
        210             215             220

Val Tyr Cys Val Gly Glu Val Asp Asn Gly Asn Pro Ala Leu Asp Cys
225             230             235             240

Pro Tyr Gln Lys Val Leu Asp Gly Val Leu Asn Tyr Pro Ile Tyr Trp
            245             250             255

Gln Leu Leu Tyr Ala Phe Glu Ser Ser Ser Gly Ser Ile Ser Asn Leu
            260             265             270

Tyr Asn Met Ile Lys Ser Val Ala Ser Asp Cys Ser Asp Pro Thr Leu
        275             280             285

Leu Gly Asn Phe Ile Glu Asn His Asp Asn Pro Arg Phe Ala Ser Tyr
        290             295             300

Thr Ser Asp Tyr Ser Gln Ala Lys Asn Val Leu Ser Tyr Ile Phe Leu
305             310             315             320

Ser Asp Gly Ile Pro Ile Val Tyr Ala Gly Glu Gln His Tyr Ser
                325             330             335

Gly Gly Lys Val Pro Tyr Asn Arg Glu Ala Thr Trp Leu Ser Gly Tyr
            340             345             350

Asp Thr Ser Ala Glu Leu Tyr Thr Trp Ile Ala Thr Asn Ala Ile
        355             360             365

Arg Lys Leu Ala Ile Ser Ala Asp Ser Ala Tyr Ile Thr Tyr Ala Asn
        370             375             380

Asp Ala Phe Tyr Thr Asp Ser Asn Thr Ile Ala Met Arg Lys Gly Thr
385             390             395             400

Ser Gly Ser Gln Val Ile Thr Val Leu Ser Asn Lys Gly Ser Ser Gly
                405             410             415

Ser Ser Tyr Thr Leu Thr Leu Ser Gly Ser Gly Tyr Thr Ser Gly Thr
            420             425             430

Lys Leu Ile Glu Ala Tyr Thr Cys Thr Ser Val Thr Val Asp Ser Ser
        435             440             445

Gly Asp Ile Pro Val Pro Met Ala Ser Gly Leu Pro Arg Val Leu Leu
        450             455             460

Pro Ala Ser Val Val Asp Ser Ser Ser Leu Cys Gly Gly Ser Gly Arg
465             470             475             480

Gly Ala Thr Ser Pro Gly Gly Ser Ser Gly Ser Val Glu Val Thr Phe
                485             490             495

Asp Val Tyr Ala Thr Thr Val Tyr Gly Gln Asn Ile Tyr Ile Thr Gly
            500             505             510

Asp Val Ser Glu Leu Gly Asn Trp Thr Pro Ala Asn Gly Val Ala Leu
        515             520             525
```

```
Ser Ser Ala Asn Tyr Pro Thr Trp Ser Ala Thr Ile Ala Leu Pro Ala
    530                 535                 540

Asp Thr Thr Ile Gln Tyr Lys Tyr Val Asn Ile Asp Gly Ser Thr Val
545                 550                 555                 560

Ile Trp Glu Asp Ala Ile Ser Asn Arg Glu Ile Thr Thr Pro Ala Ser
                565                 570                 575

Gly Thr Tyr Thr Glu Lys Asp Thr Trp Asp Glu Ser
                580                 585

<210> SEQ ID NO 40
<211> LENGTH: 1767
<212> TYPE: DNA
<213> ORGANISM: Artificial sequence
<220> FEATURE:
<223> OTHER INFORMATION: Hybrid containing A. oryzae alpha-amylase
      catalytic domain- A. rolfsii glucoamylase linker- A. rolfsii
      glucoamylase CBM
<220> FEATURE:
<221> NAME/KEY: CDS
<222> LOCATION: (1)..(1767)
<223> OTHER INFORMATION: Hybrid

<400> SEQUENCE: 40 gca acg cct gcg gac tgg cga tcg caa tcc att tat ttc ctt ctc acg    48
Ala Thr Pro Ala Asp Trp Arg Ser Gln Ser Ile Tyr Phe Leu Leu Thr
1               5                  10                  15 gat cga ttt gca agg acg gat ggg tcg acg act gcg act tgt aat act    96
Asp Arg Phe Ala Arg Thr Asp Gly Ser Thr Thr Ala Thr Cys Asn Thr
            20                  25                  30 gcg gat cag aaa tac tgt ggt gga aca tgg cag ggc atc atc gac aag   144
Ala Asp Gln Lys Tyr Cys Gly Gly Thr Trp Gln Gly Ile Ile Asp Lys
        35                  40                  45 ttg gac tat atc cag gga atg ggc ttc aca gcc atc tgg atc acc ccc   192
Leu Asp Tyr Ile Gln Gly Met Gly Phe Thr Ala Ile Trp Ile Thr Pro
    50                  55                  60 gtt aca gcc cag ctg ccc cag acc acc gca tat gga gat gcc tac cat   240
Val Thr Ala Gln Leu Pro Gln Thr Thr Ala Tyr Gly Asp Ala Tyr His
65                  70                  75                  80 ggc tac tgg cag cag gat ata tac tct ctg aac gaa aac tac ggc act   288
Gly Tyr Trp Gln Gln Asp Ile Tyr Ser Leu Asn Glu Asn Tyr Gly Thr
                85                  90                  95 gca gat gac ttg aag gcg ctc tct tcg gcc ctt cat gag agg ggg atg   336
Ala Asp Asp Leu Lys Ala Leu Ser Ser Ala Leu His Glu Arg Gly Met
            100                 105                 110 tat ctt atg gtc gat gtg gtt gct aac cat atg ggc tat gat gga gcg   384
Tyr Leu Met Val Asp Val Val Ala Asn His Met Gly Tyr Asp Gly Ala
        115                 120                 125 ggt agc tca gtc gat tac agt gtg ttt aaa ccg ttc agt tcc caa gac   432
Gly Ser Ser Val Asp Tyr Ser Val Phe Lys Pro Phe Ser Ser Gln Asp
    130                 135                 140 tac ttc cac ccg ttc tgt ttc att caa aac tat gaa gat cag act cag   480
Tyr Phe His Pro Phe Cys Phe Ile Gln Asn Tyr Glu Asp Gln Thr Gln
145                 150                 155                 160 gtt gag gat tgc tgg cta gga gat aac act gtc tcc ttg cct gat ctc   528
Val Glu Asp Cys Trp Leu Gly Asp Asn Thr Val Ser Leu Pro Asp Leu
                165                 170                 175 gat acc acc aag gat gtg gtc aag aat gaa tgg tac gac tgg gtg gga   576
Asp Thr Thr Lys Asp Val Val Lys Asn Glu Trp Tyr Asp Trp Val Gly
            180                 185                 190 tca ttg gta tcg aac tac tcc att gac ggc ctc cgt atc gac aca gta   624
Ser Leu Val Ser Asn Tyr Ser Ile Asp Gly Leu Arg Ile Asp Thr Val
        195                 200                 205
```

```
aaa cac gtc cag aag gac ttc tgg ccc ggg tac aac aaa gcc gca ggc      672
Lys His Val Gln Lys Asp Phe Trp Pro Gly Tyr Asn Lys Ala Ala Gly
    210                 215                 220 gtg tac tgt atc ggc gag gtg ctc gac ggt gat ccg gcc tac act tgt      720
Val Tyr Cys Ile Gly Glu Val Leu Asp Gly Asp Pro Ala Tyr Thr Cys
225                 230                 235                 240 ccc tac cag aac gtc atg gac ggc gta ctg aac tat ccc att tac tat      768
Pro Tyr Gln Asn Val Met Asp Gly Val Leu Asn Tyr Pro Ile Tyr Tyr
                    245                 250                 255 cca ctc ctc aac gcc ttc aag tca acc tcc ggc agc atg gac gac ctc      816
Pro Leu Leu Asn Ala Phe Lys Ser Thr Ser Gly Ser Met Asp Asp Leu
                260                 265                 270 tac aac atg atc aac acc gtc aaa tcc gac tgt cca gac tca aca ctc      864
Tyr Asn Met Ile Asn Thr Val Lys Ser Asp Cys Pro Asp Ser Thr Leu
            275                 280                 285 ctg ggc aca ttc gtc gag aac cac gac aac cca cgg ttc gct tct tac      912
Leu Gly Thr Phe Val Glu Asn His Asp Asn Pro Arg Phe Ala Ser Tyr
        290                 295                 300 acc aac gac ata gcc ctc gcc aag aac gtc gca gca ttc atc atc ctc      960
Thr Asn Asp Ile Ala Leu Ala Lys Asn Val Ala Ala Phe Ile Ile Leu
305                 310                 315                 320 aac gac gga atc ccc atc atc tac gcc ggc caa gaa cag cac tac gcc     1008
Asn Asp Gly Ile Pro Ile Ile Tyr Ala Gly Gln Glu Gln His Tyr Ala
                    325                 330                 335 ggc gga aac gac ccc gcg aac cgc gaa gca acc tgg ctc tcg ggc tac     1056
Gly Gly Asn Asp Pro Ala Asn Arg Glu Ala Thr Trp Leu Ser Gly Tyr
                340                 345                 350 ccg acc gac agc gag ctg tac aag tta att gcc tcc gcg aac gca atc     1104
Pro Thr Asp Ser Glu Leu Tyr Lys Leu Ile Ala Ser Ala Asn Ala Ile
            355                 360                 365 cgg aac tat gcc att agc aaa gat aca gga ttc gtg acc tac aag aac     1152
Arg Asn Tyr Ala Ile Ser Lys Asp Thr Gly Phe Val Thr Tyr Lys Asn
        370                 375                 380 tgg ccc atc tac aaa gac gac aca acg atc gcc atg cgc aag ggc aca     1200
Trp Pro Ile Tyr Lys Asp Asp Thr Thr Ile Ala Met Arg Lys Gly Thr
385                 390                 395                 400 gat ggg tcg cag atc gtg act atc ttg tcc aac aag ggt gct tcg ggt     1248
Asp Gly Ser Gln Ile Val Thr Ile Leu Ser Asn Lys Gly Ala Ser Gly
                    405                 410                 415 gat tcg tat acc ctc tcc ttg agt ggt gcg ggt tac aca gcc ggc cag     1296
Asp Ser Tyr Thr Leu Ser Leu Ser Gly Ala Gly Tyr Thr Ala Gly Gln
                420                 425                 430 caa ttg acg gag gtc att ggc tgc acg acc gtg acg gtt ggt tcg gat     1344
Gln Leu Thr Glu Val Ile Gly Cys Thr Thr Val Thr Val Gly Ser Asp
            435                 440                 445 gga aat gtg cct gtt cct atg gca ggt ggg cta cct agg gta ttg tat     1392
Gly Asn Val Pro Val Pro Met Ala Gly Gly Leu Pro Arg Val Leu Tyr
        450                 455                 460 ccg act gag aag ttg gca ggt agc aag atc tgt agt agc tcg gga aga     1440
Pro Thr Glu Lys Leu Ala Gly Ser Lys Ile Cys Ser Ser Ser Gly Arg
465                 470                 475                 480 ggt gct aca agc ccg ggt ggc tcc tcg ggt agt gtc gag gtc act ttc     1488
Gly Ala Thr Ser Pro Gly Gly Ser Ser Gly Ser Val Glu Val Thr Phe
                    485                 490                 495 gac gtt tac gct acc aca gta tat ggc cag aac atc tat atc acc ggt     1536
Asp Val Tyr Ala Thr Thr Val Tyr Gly Gln Asn Ile Tyr Ile Thr Gly
                500                 505                 510 gat gtg agt gag ctc ggc aac tgg aca ccc gcc aat ggt gtt gca ctc     1584
Asp Val Ser Glu Leu Gly Asn Trp Thr Pro Ala Asn Gly Val Ala Leu
            515                 520                 525
```

```
tct tct gct aac tac ccc acc tgg agt gcc acg atc gct ctc ccc gct    1632
Ser Ser Ala Asn Tyr Pro Thr Trp Ser Ala Thr Ile Ala Leu Pro Ala
530                 535                 540 gac acg aca atc cag tac aag tat gtc aac att gac ggc agc acc gtc    1680
Asp Thr Thr Ile Gln Tyr Lys Tyr Val Asn Ile Asp Gly Ser Thr Val
545                 550                 555                 560 atc tgg gag gat gct atc agc aat cgc gag atc acg acg ccc gcc agc    1728
Ile Trp Glu Asp Ala Ile Ser Asn Arg Glu Ile Thr Thr Pro Ala Ser
                565                 570                 575 ggc aca tac acc gaa aaa gac act tgg gat gaa tct tag                1767
Gly Thr Tyr Thr Glu Lys Asp Thr Trp Asp Glu Ser
                580                 585
```

<210> SEQ ID NO 41
<211> LENGTH: 588
<212> TYPE: PRT
<213> ORGANISM: Artificial sequence
<220> FEATURE:
<223> OTHER INFORMATION: Synthetic Construct

<400> SEQUENCE: 41

```
Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ala Leu His Glu Arg Gly Met
            100                 105                 110

Tyr Leu Met Val Asp Val Val Ala Asn His Met Gly Tyr Asp Gly Ala
        115                 120                 125

Gly Ser Ser Val Asp Tyr Ser Val Phe Lys Pro Phe Ser Ser Gln Asp
    130                 135                 140

Tyr Phe His Pro Phe Cys Phe Ile Gln Asn Tyr Glu Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
    210                 215                 220

Val Tyr Cys Ile Gly Glu Val Leu Asp Gly Asp Pro Ala Tyr Thr Cys
225                 230                 235                 240

Pro Tyr Gln Asn Val Met Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270

Tyr Asn Met Ile Asn Thr Val Lys Ser Asp Cys Pro Asp Ser Thr Leu
        275                 280                 285
```

-continued

```
Leu Gly Thr Phe Val Glu Asn His Asp Asn Pro Arg Phe Ala Ser Tyr
    290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
                325                 330                 335

Gly Gly Asn Asp Pro Ala Asn Arg Glu Ala Thr Trp Leu Ser Gly Tyr
                340                 345                 350

Pro Thr Asp Ser Glu Leu Tyr Lys Leu Ile Ala Ser Ala Asn Ala Ile
            355                 360                 365

Arg Asn Tyr Ala Ile Ser Lys Asp Thr Gly Phe Val Thr Tyr Lys Asn
    370                 375                 380

Trp Pro Ile Tyr Lys Asp Asp Thr Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
                420                 425                 430

Gln Leu Thr Glu Val Ile Gly Cys Thr Thr Val Thr Val Gly Ser Asp
            435                 440                 445

Gly Asn Val Pro Val Pro Met Ala Gly Gly Leu Pro Arg Val Leu Tyr
    450                 455                 460

Pro Thr Glu Lys Leu Ala Gly Ser Lys Ile Cys Ser Ser Ser Gly Arg
465                 470                 475                 480

Gly Ala Thr Ser Pro Gly Gly Ser Ser Gly Ser Val Glu Val Thr Phe
                485                 490                 495

Asp Val Tyr Ala Thr Thr Val Tyr Gly Gln Asn Ile Tyr Ile Thr Gly
                500                 505                 510

Asp Val Ser Glu Leu Gly Asn Trp Thr Pro Ala Asn Gly Val Ala Leu
            515                 520                 525

Ser Ser Ala Asn Tyr Pro Thr Trp Ser Ala Thr Ile Ala Leu Pro Ala
    530                 535                 540

Asp Thr Thr Ile Gln Tyr Lys Tyr Val Asn Ile Asp Gly Ser Thr Val
545                 550                 555                 560

Ile Trp Glu Asp Ala Ile Ser Asn Arg Glu Ile Thr Thr Pro Ala Ser
                565                 570                 575

Gly Thr Tyr Thr Glu Lys Asp Thr Trp Asp Glu Ser
                580                 585
```

PROCESSES FOR PRODUCING A FERMENTATION PRODUCT

CROSS-REFERENCE TO RELATED APPLICATIONS

This application is a continuation of U.S. application Ser. No. 10/586,109 filed on Oct. 31, 2006, now abandoned, which is a 35 U.S.C. 371 national application of PCT/US2005/001147 filed Jan. 14, 2005, which claims priority or the benefit under 35 U.S.C. 119 of U.S. provisional application Nos. 60/537,071 and 60/636,013 filed Jan. 16, 2004 and Dec. 14, 2004, respectively, the contents of which are fully incorporated herein by reference.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to processes for production of a fermentation product from milled starch-containing material, such as granular starch, at a temperature below the initial gelatinization temperature of the milled starch-containing material in the presence of glucoamylase.

2. Description of Related Art

Grains, cereals or tubers of plants contain starch. The starch is in the form of microscopic granules, which are insoluble in water at room temperature. When an aqueous starch slurry is heated, the granules swell and eventually burst, dispersing the starch molecules into the solution. During this "gelatinization" process, there is a dramatic increase in viscosity. Because the solids level in a typical industrial process is around 30-40%, the starch has to be thinned or "liquefied" so that it can be handled. This reduction in viscosity is generally accomplished by enzymatic degradation in a process referred to as liquefaction. During liquefaction, the long-chained starch is degraded into smaller branched and linear chains of glucose units (dextrins) by an alpha-amylase.

A conventional enzymatic liquefaction process may be carried out as a three-step hot slurry process. The slurry is heated to between 80-85° C. and thermostable alpha-amylase added to initiate liquefaction. The slurry is then jet-cooked at a temperature between 105-125° C. to complete gelatinization of the slurry, cooled to 60-95° C. and, generally, additional alpha-amylase is added to finalize hydrolysis. The liquefaction process is generally carried out at pH between 5 and 6. Milled and liquefied whole grains are known as mash.

During saccharification, the dextrins from the liquefaction are further hydrolyzed to produce low molecular sugars $DP_{1-3}$ that can be metabolized by a fermenting organism, such as yeast. The hydrolysis is typically accomplished using glucoamylase, alternatively or in addition to glucoamylases, alpha-glucosidases and/or acid alpha-amylases can be used. A full saccharification step typically last up to 72 hours, however, it is common only to do a pre-saccharification of, e.g., 40-90 minutes at a temperature above 50° C., followed by a complete saccharification during fermentation in a process known as simultaneous saccharification and fermentation (SSF).

Fermentation is performed using a fermenting organism, such as yeast, which is added to the mash. Then the fermentation product is recovered. For ethanol, e.g. fuel, potable, or industrial ethanol, the fermentation is carried out, for typically 35-60 hours at a temperature of typically around 32° C. When the fermentation product is beer, the fermentation is carried out, for typically up to 8 days at a temperature of typically around 14° C.

Following fermentation, the mash may be used, e.g., as a beer, or distilled to recover ethanol. The ethanol may be used as, e.g., fuel ethanol, drinking ethanol, and/or industrial ethanol.

It will be apparent from the above discussion that the starch hydrolysis in a conventional process is very energy consuming due to the different temperature requirements during the various steps.

U.S. Pat. No. 4,316,956 provides a fermentation process for conversion of granular starch into ethanol.

European Patent No. 140410 provides an enzyme composition for starch hydrolysis.

WO 2004/081193 concerns a method of producing high levels of alcohol during fermentation of plant material. The method includes i) preparing the plant material for saccharification, ii) converting the prepared plant material to sugar without cooking, and iii) fermenting the sugars.

The object of the present invention is to provide improved processes for conversion of milled starch-containing material, such as granular starch, into a fermentation product, such as ethanol.

SUMMARY OF THE INVENTION

The present invention provides processes of producing a fermentation product from starch-containing material without gelatinization of said starch-containing material using glucoamylase.

In the first aspect, the invention provides a process for producing a fermentation product from milled starch-containing material comprising:

(a) saccharifying milled starch-containing material with a glucoamylase having an amino acid sequence shown in SEQ ID NO: 2, or a glucoamylase being at least 70% identical thereto, at a temperature below the initial gelatinization temperature of said starch-containing material, (b) fermenting using a fermenting organism.

Steps (a) and (b) may be carried out sequentially or simultaneously.

Preferably, a slurry comprising water and milled starch-containing material is prepared before step (a). The dry solid content (DS) lies in the range from 20-55 wt.-%. In order to expose more surface of the starch-containing material it is milled. In an embodiment the particle size is between 0.05-3.0 mm, or at least 30% of the milled starch-containing material fit through a sieve with a 0.05 to 3.0 mm screen. The process of the invention may be carried out for a period of 1 to 250 hours. The pH during saccharification and/or fermentation may be in the range from between 3 and 7. During fermentation the glucose concentration may be kept at a level of below about 3 wt.-%. In a preferred embodiment saccharification and fermentation is carried out simultaneously. According to a preferred embodiment the glucoamylase is derived from a strain of *Athelia*, preferably a strain of *Athelia rolfsii*. The glucoamylase is present in an amount of 0.001 to 10 AGU/g DS. In a preferred embodiment an acid alpha-amylase is present as well. The acid alpha-amylase may be a fungal or bacterial alpha-amylase, preferably a fungal alpha-amylase derived from a strain of *Aspergillus*, especially *A. niger* or *A. oryzae*. The acid alpha-amylase may be present in a concentration of 0.1 to 10 AFAU/g DS. The ratio between acid alpha-amylase and glucoamylase may be between 0.1 and 10 AGU/AFAU. Optionally the fermentation product, such as ethanol, is recovered after fermentation. Other ingredients and enzyme activities may also be present during the process of the invention. Examples of other enzyme activities are xylanase, cellulase, and phytase activity.

DETAILED DESCRIPTION OF THE INVENTION

The present invention provides processes for producing a fermentation product from starch-containing material without gelatinization of said starch-containing material. In one embodiment only a glucoamylase is needed during saccharification and fermentation. According to the invention the desired fermentation product, such as ethanol, can be produced without liquefying the aqueous slurry containing the starch-containing material. If the aqueous slurry containing starch-containing material is heated to above the gelatinization temperature liquefaction is necessary. In general a process of the invention includes saccharifying milled starch-containing material below the gelatinization temperature in the presence of a glucoamylase having the sequence shown in SEQ ID NO: 2, or homologues thereto, to produce sugars that can be fermented into the desired fermentation product by a suitable fermenting organism.

The inventors have found that when producing ethanol from uncooked milled corn using the glucoamylase derived from *Athelia rolfsii* shown in SEQ ID NO: 2 a significantly higher ethanol yield is obtained compared to a corresponding process using glucoamylase derived from *Aspergillus niger* or *Talaromyces emersonii*. When adding fungal acid alpha-amylase from *Aspergillus niger* (SEQ ID NO: 3) to the process the performance is still significantly higher, i.e., compared to a corresponding process using the *Aspergillus niger* glucoamylase and fungal acid alpha-amylase derived from *Aspergillus niger*.

Accordingly, in the first aspect the invention relates to a process for producing a fermentation product from milled starch-containing material comprising:

(a) saccharifying milled starch-containing material with a glucoamylase having an amino acid sequence shown in SEQ ID NO: 2, or a glucoamylase being at least 70% identical thereto, at a temperature below the initial gelatinization temperature of said starch-containing material, (b) fermenting using a fermenting organism.

Steps (a) and (b) of the process of the invention may be carried out sequentially or simultaneously.

Before step (a), a slurry of starch-containing material, such as granular starch, having 20-55 wt.-% dry solids, preferably 25-40 wt.-% dry solids, more preferably 30-35% dry solids of starch-containing material may be prepared. The slurry may include water and/or process waters, such as stillage (backset), scrubber water, evaporator condensate or distillate, side stripper water from distillation, or other fermentation product plant process water. Because the process of the invention is carried out below the gelatinization temperature and thus no significant viscosity increase takes place high levels of stillage may be used if desired. In an embodiment the aqueous slurry contains from about 1 to about 70 vol.-% stillage, preferably 15-60% vol.-% stillage, especially from about 30 to 50 vol.-% stillage.

The milled starch-containing material may be prepared by milling starch-containing material to a particle size of 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the starch-containing material is converted into a soluble starch hydrolysate.

The process of the invention is conducted at a temperature below the initial gelatinization temperature. Preferably the temperature at which step (a) is carried out is between 30-75° C., preferably between 45-60° C.

In a preferred embodiment, steps (a) and (b) are carried out as a simultaneous saccharification and fermentation process. In such preferred embodiment the process is typically carried at a temperature between 28° C. and 36° C., such as between 29° C. and 35° C., such as between 30° C. and 34° C., such as around 32° C. According to the invention the temperature may be adjusted up or down during fermentation.

In an embodiment simultaneous saccharification and fermentation is carried out so that the sugar level, such as glucose level, is kept at a low level such as below about 3 wt.-%, preferably below about 2 wt.-%, more preferred below about 1 wt.-%., even more preferred below about 0.5%, or even more preferred below about 0.1 wt.-%. Such low levels of sugar can be accomplished by simply employing adjusted quantities of enzyme and fermenting organism. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt.-% or below about 0.2 wt.-%.

The process of the invention may be carried out at a pH in the range between 3 and 7, preferably from 3.5 to 6, or more preferably from 4 to 5.

Starch-Containing Materials

Any suitable starch-containing starting material, including granular starch, may be used according to the present invention. The starting material is generally selected based on the desired fermentation product. Examples of starch-containing starting materials, suitable for use in the processes of present invention, include tubers, roots, stems, whole grains, corns, cobs, wheat, barley, rye, milo, sago, cassava, tapioca, sorghum, rice peas, beans, or cereals, sugar-containing raw materials, such as molasses, fruit materials, sugar, cane or sugar beet, potatoes, and cellulose-containing materials, such as wood or plant residues. Contemplated are both waxy and non-waxy types of corn and barley.

The term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch containing material comprising milled whole grain including non-starch fractions such as germ residues and fibers. The raw material, such as whole grain, is milled in order to open up the structure and allowing for further processing. Two milling processes are preferred according to the invention: wet and dry milling. In dry milling whole kernels are milled and used. Wet milling gives a good separation of germ and meal (starch granules and protein) and is often applied at locations where the starch hydrolysate is used in production of syrups. Both dry and wet milling is well known in the art of starch processing and is equally contemplated for the process of the invention.

The starch-containing material is milled in order to expose more surface. In an embodiment the particle size is between 0.05 to 3.0 mm, or so that at least 30%, preferably at least 50%, more preferably at least 70%, even more preferably at least 90% of the milled starch-containing material fit through a sieve with a 0.05 to 3.0 mm screen, preferably 0.1-0.5 mm screen.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein and Lii, 1992, Starch/Stärke 44(12): 461-466.

Fermentation Product

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes, as are well known in the art. Preferred fermentation processes are anaerobic fermentation processes, as are well known in the art.

Fermenting Organism

"Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include fungal organisms, such as yeast. Preferred yeast includes strains of the Saccharomyces spp., and in particular, Saccharomyces cerevisiae. Commercially available yeast include, e.g., Red Star™/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Glucoamylase

The term "glucoamylase activity" means a glucan 1,4-alpha-glucosidase which hydrolyses the terminal 1,4-linked alpha-D-glucose residues successively from non-reducing ends of the chains with release of beta-D-glucose belonging to the Enzyme Class EC 3.2.1.3.

The glucoamylase used in a process of the invention has the amino acid sequence shown in SEQ ID NO: 2 (amino acid residues 1 to 561), or an amino acid sequence that is at least 70%, preferably at least 75%, or at least 80%, or at least 85%, or 90%, or at least 95%, at least 96%, at least 97%, at least 98% or even at least 99% identical to SEQ ID NO: 2 (amino acid residues 1 to 561). The glucoamylase derived from Athelia rolfsii, the amino acid sequence of which is available as SPTREMBL:Q12596, is almost identical to the one shown in SEQ ID NO: 2, except for one amino acid residue corresponding to the amino acid residue in position 97 of SEQ ID NO: 2, which in the database sequence is a serine, whereas in SEQ ID NO: 2 it is a proline. The annotation of the database sequence identifies amino acid residues 1-18 as a signal peptide, and residues 19-579 (i.e., 561 amino acid residues) as the mature glucoamylase enzyme, with residues 472-482 serving as a linker between the glucoamylase domain and the starch-binding domain comprised in residues 483-579.

The glucoamylase may in an embodiment be added in an amount of 0.001 to 10 AGU/g DS, preferably from 0.01 to 5 AGU/g DS, such as around 0.1, 0.3, 0.5, 1 or 2 AGU/g DS, especially 0.1 to 0.5 AGU/g DS or 0.02-20 AGU/g DS, preferably 0.1-10 AGU/g DS.

Alpha-Amylase

In a preferred embodiment an alpha-amylase may be added to the process of the invention. The alpha-amylase may according to the invention be of any origin. Preferred are alpha-amylases of fungal or bacterial origin.

In a preferred embodiment the alpha-amylase is an acid alpha-amylase, e.g., fungal acid alpha-amylase or bacterial acid alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylases

According to the invention the bacterial alpha-amylase may be derived from the genus Bacillus.

In a preferred embodiment the Bacillus alpha-amylase is derived from a strain of B. licheniformis, B. amyloliquefaciens, B. subtilis or B. stearothermophilus, but may also be derived from other Bacillus sp. Specific examples of contemplated alpha-amylases include the Bacillus licheniformis alpha-amylase (BLA) shown in SEQ ID NO: 5, the Bacillus amyloliquefaciens alpha-amylase (BAN) shown in SEQ ID NO: 6, and the Bacillus stearothermophilus alpha-amylase (BSG) shown in SEQ ID NO: 7. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 98% or at least 99% identity to any of the sequences shown in SEQ ID NO: 5, 6, or 7 of the present application or SEQ ID NO: 1, 2 or 3 in WO 99/19467.

The Bacillus alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,187,576, and 6,297,038 (hereby incorporated by reference) and include Bacillus stearothermophilus alpha-amylase (BSG alpha-amylase) variants having a double deletion disclosed in WO 1996/023873—see e.g., page 20, lines 1-10 (hereby incorporated by reference), preferably corresponding to delta(181-182) compared to the wild-type BSG alpha-amylase amino acid sequence set forth in SEQ ID NO: 7 disclosed in WO 99/19467 (hereby incorporated by reference). Even more preferred are Bacillus alpha-amylases, especially Bacillus stearothermophilus alpha-amylase, which have a double deletion corresponding to delta(181-182) and further comprise a N193F substitution (also denoted I181*+G182*+

N193F) compared to the wild-type BSG alpha-amylase amino acid sequence set forth in SEQ ID NO: 7 of the present application and SEQ ID NO: 3 disclosed in WO 99/19467.

The alpha-amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic alpha-amylase from *Bacillus stearothermophilus* strain NCIB 11837 is commercially available from Novozymes NS, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the *Bacillus licheniformis* alpha-amylase (shown in SEQ ID NO: 5) and the 37 N-terminal amino acid residues of the alpha-amylase derived from *Bacillus amyloliquefaciens* (shown in SEQ ID NO: 6), with one or more, especially all, of the following substitution:

G48A+T49I+G107A+H156Y+A181T+N190F+1201F+ A209V+Q264S (using the *Bacillus licheniformis* numbering). Also preferred are variants having one or more of the following mutations (or corresponding mutations in other *Bacillus* alpha-amylase backbones): H154Y, A181T, N190F, A209V and Q264S and/ or deletion of two residues between positions 176 and 179, preferably deletion of E178 and G179 (using the SEQ ID NO: 5 numbering of WO 99/19467).

The bacterial alpha-amylase may be added in amounts as are well-known in the art. When measured in KNU units (described below in the Materials & Methods"-section) the alpha-amylase activity is preferably present in an amount of 0.5-5,000 NU/g of DS, in an amount of 1-500 NU/g of DS, or more preferably in an amount of 5-1,000 NU/g of DS, such as 10-100 NU/g DS.

Fungal Alpha-Amylases

Fungal acid alpha-amylases include acid alpha-amylases derived from a strain of the genus *Aspergillus*, such as, *Aspergillus oryzae* and *Aspergillus niger* alpha-amylases.

A preferred acid fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874 or shown as SEQ ID NO: 4 of the present application.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 3. Also variants of said acid fungal amylase having at least 70% identity, such as at least 80% or even at least 90% identity, such as at least 95%, 96%, 97%, 98%, or at least 99% identity to SEQ ID NO: 3 are contemplated. A commercially available acid fungal alpha-amylase derived from *Aspergillus niger* is SP288 (available from Novozymes NS, Denmark).

The fungal acid alpha-amylase may also be a wild-type enzyme comprising a carbohydrate-binding module (CBM) and an alpha-amylase catalytic domain (i.e., none-hybrid), or a variant thereof. In an embodiment the wild-type acid alpha-amylase is derived from a strain of *Aspergillus kawachi*, in particular the alpha-amylase shown in SEQ ID NO: 31. Also variants of said fungal acid amylase having at least 70% identity, such as at least 80% or even at least 90% identity, such as at least 95%, at least 96%, at least 97%, at least 98%, or at least 99% identity to SEQ ID NO: 31 are contemplated.

Fungal Hybrid Alpha-Amylases

In a preferred embodiment the fungal acid alpha-amylase is a hybrid alpha-amylase. Preferred examples of fungal hybrid alpha-amylases include the ones disclosed in PCT/ US2004/020499 (Novozymes), which is hereby incorporated by reference. A hybrid alpha-amylase may comprise an alpha-amylase catalytic domain (CD) and a carbohydrate-binding module (CBM) and optional a linker.

Hybrid enzymes or a genetically modified wild-type enzymes, as referred to herein, include species comprising an amino acid sequence of an alpha-amylase enzyme (EC 3.2.1.1) linked (i.e., covalently bound) to an amino acid sequence comprising a carbohydrate-binding module (CBM).

CBM-containing hybrid enzymes, as well as detailed descriptions of the preparation and purification thereof, are known in the art [see, e.g. WO 90/00609, WO 94/24158 and WO 95/16782, as well as Greenwood et al., 1994, Biotechnology and Bioengineering 44: 1295-1305]. They may, e.g., be prepared by transforming into a host cell a DNA construct comprising at least a fragment of DNA encoding the carbohydrate-binding module ligated, with or without a linker, to a DNA sequence encoding the enzyme of interest, and growing the transformed host cell to express the fused gene. The resulting recombinant product (hybrid enzyme)—often referred to in the art as a "fusion protein—may be described by the following general formula:

A-CBM-MR-X

In the latter formula, A-CBM is the N-terminal or the C-terminal region of an amino acid sequence comprising at least the carbohydrate-binding module (CBM) per se. MR is the middle region (the "linker"), and X is the sequence of amino acid residues of a polypeptide encoded by a DNA sequence encoding the enzyme (or other protein) to which the CBM is to be linked.

The moiety A may either be absent (such that A-CBM is a CBM per se, i.e. comprises no amino acid residues other than those constituting the CBM) or may be a sequence of one or more amino acid residues (functioning as a terminal extension of the CBM per se). The linker (MR) may be a bond, or a short linking group comprising from about 2 to about 100 carbon atoms, in particular of from 2 to 40 carbon atoms. However, MR is preferably a sequence of from about 2 to about 100 amino acid residues, more preferably of from 2 to 40 amino acid residues, such as from 2 to 15 amino acid residues.

The moiety X may constitute either the N-terminal or the C-terminal region of the overall hybrid enzyme.

It will thus be apparent from the above that the CBM in a hybrid enzyme of the type in question may be positioned C-terminally, N-terminally or internally in the hybrid enzyme.

Linker Sequence

The optional linker sequence may be any suitable linker sequence. In preferred embodiments the linker sequence is derived from the *Athelia rolfsii* glucoamylase, the *A. niger* glucoamylase or the *A. kawachii* alpha-amylase such as a linker sequence selected from the group consisting of *A. niger* glucoamylase linker: TGGTTTTATPTGSGSVTSTSKT- TATASKTSTSTSSTSA (SEQ ID NO: 8), *A. kawachii* alpha-amylase linker: TTTTTTAAATSTSKATTSSSSS-SAAATTSSS (SEQ ID NO: 9), *Athelia rolfsii* glucoamylase linker: GATSPGGSSGS (SEQ ID NO: 10), and the PEPT linker: PEPTPEPT (SEQ ID NO: 11). In another preferred embodiment the hybrid enzymes has a linker sequence which differs from the amino acid sequence shown in SEQ ID NO: 8, SEQ ID NO: 9, SEQ ID NO: 10, or SEQ ID NO: 11 in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Carbohydrate-Binding Modules

A carbohydrate-binding module (CBM), or as often referred to, a carbohydrate-binding domain (CBD), is a polypeptide amino acid sequence which binds preferentially to a poly- or oligosaccharide (carbohydrate), frequently—but not necessarily exclusively—to a water-insoluble (including crystalline) form thereof.

CBMs derived from starch degrading enzymes are often referred to as starch-binding modules or SBMs (CBMs which may occur in certain amylolytic enzymes, such as certain glucoamylases, or in enzymes such as cyclodextrin glucanotransferases, or in alpha-amylases). Likewise, other subclasses of CBMs would embrace, e.g., cellulose-binding modules (CBMs from cellulolytic enzymes), chitin-binding modules (CBMs which typically occur in chitinases), xylan-binding modules (CBMs which typically occur in xylanases), mannan-binding modules (CBMs which typically occur in mannanases). SBMs are often referred to as SBDs (Starch Binding Domains).

CBMs are found as integral parts of large polypeptides or proteins consisting of two or more polypeptide amino acid sequence regions, especially in hydrolytic enzymes (hydrolases) which typically comprise a catalytic module containing the active site for substrate hydrolysis and a carbohydrate-binding module (CBM) for binding to the carbohydrate substrate in question. Such enzymes can comprise more than one catalytic module and one, two or three CBMs, and optionally further comprise one or more polypeptide amino acid sequence regions linking the CBM(s) with the catalytic module(s), a region of the latter type usually being denoted a "linker". Examples of hydrolytic enzymes comprising a CBM—some of which have already been mentioned above—are cellulases, xylanases, mannanases, arabinofuranosidases, acetylesterases and chitinases. CBMs have also been found in algae, e.g., in the red alga *Porphyra purpurea* in the form of a non-hydrolytic polysaccharide-binding protein.

In proteins/polypeptides in which CBMs occur (e.g., enzymes, typically hydrolytic enzymes), a CBM may be located at the N or C terminus or at an internal position.

That part of a polypeptide or protein (e.g., hydrolytic enzyme) which constitutes a CBM per se typically consists of more than about 30 and less than about 250 amino acid residues.

The "Carbohydrate-Binding Module of Family 20" or a CBM-20 module is in the context of this invention defined as a sequence of approximately 100 amino acids having at least 45% identity to the Carbohydrate-Binding Module (CBM) of the polypeptide disclosed in FIG. 1 by Joergensen et al., 1997, *Biotechnol. Lett.* 19:1027-1031. The CBM comprises the last 102 amino acids of the polypeptide, i.e., the subsequence from amino acid 582 to amino acid 683. The numbering of Glycoside Hydrolase Families applied in this disclosure follows the concept of Coutinho, P. M. & Henrissat, B. (1999) *CAZy—Carbohydrate-Active Enzymes server* on the internet or alternatively Coutinho, P. M. & Henrissat, B. 1999; The modular structure of cellulases and other carbohydrate-active enzymes: an integrated database approach. In "*Genetics, Biochemistry and Ecology of Cellulose Degradation*", K. Ohmiya, K. Hayashi, K. Sakka, Y. Kobayashi, S. Karita and T. Kimura eds., Uni Publishers Co., Tokyo, pp. 15-23, and Bourne, Y. & Henrissat, B. 2001; Glycoside hydrolases and glycosyltransferases: families and functional modules, *Current Opinion in Structural Biology* 11:593-600.

Examples of enzymes which comprise a CBM suitable for use in the context of the invention are alpha-amylases, maltogenic alpha-amylases, cellulases, xylanases, mannanases, arabinofuranosidases, acetylesterases and chitinases. Further CBMs of interest in relation to the present invention include CBMs deriving from glucoamylases (EC 3.2.1.3) or from CGTases (EC 2.4.1.19).

CBMs deriving from fungal, bacterial or plant sources will generally be suitable for use in the context of the invention. Preferred are CBMs of fungal origin, more preferably from *Aspergillus* sp., *Bacillus* sp., *Klebsiella* sp., or *Rhizopus* sp. In this connection, techniques suitable for isolating the relevant genes are well known in the art.

Preferred for the invention is CBMs of Carbohydrate-Binding Module Family 20. CBMs of Carbohydrate-Binding Module Family 20 suitable for the invention may be derived from glucoamylases of *Aspergillus awamori* (SWISSPROT Q12537), *Aspergillus kawachii* (SWISSPROT P23176), *Aspergillus niger* (SWISSPROT PO4064), *Aspergillus oryzae* (SWISSPROT P36914), from alpha-amylases of *Aspergillus kawachii* (EMBL:#AB008370), *Aspergillus nidulans* (NCBI AAF17100.1), from beta-amylases of *Bacillus cereus* (SWISSPROT P36924), or from CGTases of *Bacillus circulans* (SWISSPROT P43379). Preferred is a CBM from the alpha-amylase of *Aspergillus kawachii* (EMBL:#AB008370) as well as CBMs having at least 50%, at least 60%, at least 70%, at least 80%, at least 90%, at least 95, at least 96%, at least 97%, at least 98% or even at least 99% identity to the CBM of the alpha-amylase of *Aspergillus kawachii* (EMBL:#AB008370), i.e., a CBM having at least 50%, 60%, 70%, 80%, 95%, 96%, 97%, 98% or even at least 99% identity to the amino acid sequence of SEQ ID NO: 12. Also preferred for the invention are the CBMs of Carbohydrate-Binding Module Family 20 having the amino acid sequences shown in SEQ ID NO: 14 (*Bacillus flavothermus* CBM), SEQ ID NO: 15 (*Bacillus* sp. CBM), and SEQ ID NO: 16 (Alcaliphilic *Bacillus* CBM) and disclosed in International application PCT/DK2004/000456 as SEQ ID NO: 1, SEQ ID NO: 2 and SEQ ID NO: 3 respectively. Further preferred CBMs include the CBMs of the glucoamylase from *Hormoconis* sp. such as from *Hormoconis resinae* (Syn. Creosote fungus or *Amorphotheca resinae*) such as the CBM of SWISSPROT Q03045 (SEQ ID NO: 17), from *Lentinula* sp. such as from *Lentinula edodes* (shiitake mushroom) such as the CBM of SPTREMBL:Q9P4C5 (SEQ ID NO: 18), from *Neurospora* sp. such as from *Neurospora crassa* such as the CBM of SWISSPROT P14804 (SEQ ID NO: 19), from *Talaromyces* sp. such as from *Talaromyces byssochlamydioides* such as the CBM of NN005220 (SEQ ID NO: 20), from *Geosmithia* sp. such as from *Geosmithia cylindrospora*, such as the CBM of NN48286 (SEQ ID NO: 21), from *Scorias* sp. such as from *Scorias spongiosa* such as the CBM of NN007096 (SEQ ID NO: 22), from *Eupenicillium* sp. such as from *Eupenicillium ludwigii* such as the CBM of NN005968 (SEQ ID NO: 23), from *Aspergillus* sp. such as from *Aspergillus japonicus* such as the CBM of NN001136 (SEQ ID NO: 24), from *Penicillium* sp. such as from *Penicillium* cf. *miczynskii* such as the CBM of NN48691 (SEQ ID NO: 25), from Mz1 *Penicillium* sp. such as the CBM of NN48690 (SEQ ID NO: 26), from *Thysanophora* sp. such as the CBM of NN48711 (SEQ ID NO: 27), and from *Humicola* sp. such as from *Humicola grisea* var. *thermoidea* such as the CBM of SPTREMBL: Q12623 (SEQ ID NO: 28). Most preferred CBMs include the CBMs of the glucoamylase from *Aspergillus* sp. such as from *Aspergillus niger*, such as SEQ ID NO: 29, and *Athelia* sp. such as from *Athelia rolfsii*, such as SEQ ID NO: 30.

Preferably the hybrid enzyme comprises a CBM sequence having at least 50%, at least 60%, at least 70%, at least 80% at least 90%, at least 95%, at least 96%, at least 97%, at least 98% or even at least 99% identity to any of the amino acid sequences shown in SEQ ID NO: 13, SEQ ID NO: 14 10, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or SEQ ID NO: 30. In yet another preferred embodiment the CBM sequence has an amino acid sequence which differs from the amino acid sequence amino acid sequence shown in SEQ ID NO: 13, SEQ ID NO: 14 10, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or SEQ ID NO: 30 in no more than 10 amino acid positions, no more than 9 positions, no more than 8 positions, no more than 7 positions, no more than 6 positions, no more than 5 positions, no more than 4 positions, no more than 3 positions, no more than 2 positions, or even no more than 1 position. In a most preferred embodiment the hybrid enzyme comprises a CBM derived from a glucoamylase from *Athelia rolfsii*, such as the glucoamylase from *A. rolfsii* AHU 9627 described in U.S. Pat. No. 4,727,026.

Further suitable CBMs of Carbohydrate-Binding Module Family 20 may be found on the internet.

Once a nucleotide sequence encoding the substrate-binding (carbohydrate-binding) region has been identified, either as cDNA or chromosomal DNA, it may then be manipulated in a variety of ways to fuse it to a DNA sequence encoding the enzyme of interest. The DNA fragment encoding the carbohydrate-binding amino acid sequence, and the DNA encoding the enzyme of interest are then ligated with or without a linker. The resulting ligated DNA may then be manipulated in a variety of ways to achieve expression.

Catalytic Domain in Hybrid

Alpha-amylases (in particular acid alpha-amylases) which are appropriate as the basis for CBM/amylase hybrids of the types employed in the context of the present invention include those of fungal origin. Preferred examples are the ones described above in the "fungal alpha-amylases"-section, which include acid alpha-amylases from *Aspergillus niger* shown as SEQ ID NO: 3 or *Aspergillus oryzae* shown in SEQ ID NO: 4.

Even more preferred is an embodiment wherein the hybrid enzyme comprises an alpha-amylase sequence derived from the *A. oryzae* acid alpha-amylase (Fungamyl™, SEQ ID NO: 4), and/or a linker sequence derived from the *A. kawachii* alpha-amylase (SEQ ID NO: 9 or the *A. rolfsii* glucoamylase (SEQ ID NO: 10), and/or a CBM derived from the *A. kawachii* alpha-amylase (SEQ ID NO: 13) or the *A. rolfsii* glucoamylase (SEQ ID NO: 30).

Also preferred is an embodiment wherein the hybrid enzyme comprises an alpha-amylase sequence derived from the *A. niger* acid alpha-amylase (SP288) catalytic module having the sequence shown in SEQ ID NO: 3, and/or a linker sequence derived from the *A. kawachii* alpha-amylase (SEQ ID NO: 9) or the *A. rolfsii* glucoamylase (SEQ ID NO: 10), and/or the CBM derived from the *A. kawachii* alpha-amylase (SEQ ID NO: 12), the *A. rolfsii* glucoamylase (SEQ ID NO: 30) or the *A. niger* glucoamylase (SEQ ID NO: 29). In a particularly preferred embodiment the hybrid enzyme comprises the *A. niger* acid alpha-amylase (SP288) catalytic module having the sequence shown in SEQ ID NO: 3 and the *A. kawachii* alpha-amylase linker (SEQ ID NO: 9) and CBM (SEQ ID NO: 12).

In a specific embodiment the hybrid enzyme is the mature part of the amino acid sequence shown in SEQ ID NO: 33 (*A. niger* acid alpha-amylase catalytic domain-*A. kawachii* alpha-amylase linker-*A. niger* glucoamylase CBM), SEQ ID NO: 35 (*A. niger* acid alpha-amylase catalytic domain-*A. kawachii* alpha-amylase linker-*A. rolfsii* glucoamylase CBM), or SEQ ID NO: 37 (*A. oryzae* acid alpha-amylase catalytic domain-*A. kawachii* alpha-amylase linker-*A. kawachii* alpha-amylase CBM), or SEQ ID NO: 39 (*A. niger* acid alpha-amylase catalytic domain-*A. rolfsii* glucoamylase linker-*A. rolfsii* glucoamylase CBM), or SEQ ID NO: 41 (*A. oryzae* acid alpha-amylase catalytic domain-*A. rolfsii* glucoamylase linker-*A. rolfsii* glucoamylase CBM) or the hybrid consisting of *A. niger* acid alpha-amylase catalytic domain (SEQ ID NO: 3)-*A. kawachii* alpha-amylase linker (SEQ ID NO: 9)—*A. kawachii* alpha-amylase CBM (SEQ ID NO: 13) or a hybrid enzyme that has an amino acid sequence having at least 50%, at least 60%, at least 70%, at least 80%, or even at least 90%, at least 95%, at least 96%, at least 97%, at least 98%, or at least 99% identity to any of the afore mentioned amino acid sequences.

In another preferred embodiment the hybrid enzyme has an amino acid sequence which differs from the amino acid sequence amino acid sequence shown in SEQ ID NO: 33 (*A. niger* acid alpha-amylase catalytic domain-*A. kawachii* alpha-amylase linker-*A. niger* glucoamylase CBM), SEQ ID NO: 35 (*A. niger* acid alpha-amylase catalytic domain-*A. kawachii* alpha-amylase linker-*A. rolfsii* glucoamylase CBM), SEQ ID NO: 37 (*A. oryzae* acid alpha-amylase catalytic domain-*A. kawachii* alpha-amylase linker-*A. kawachii* alpha-amylase CBM), SEQ ID NO: 39 (*A. niger* acid alpha-amylase catalytic domain-*A. rolfsii* glucoamylase linker-*A. rolfsii* glucoamylase CBM) or SEQ ID NO: 41 (*A. oryzae* acid alpha-amylase catalytic domain-*A. rolfsii* glucoamylase linker-*A. rolfsii* glucoamylase CBM) or the hybrid consisting of *A. niger* acid alpha-amylase catalytic domain (SEQ ID NO: 3)—*A. kawachii* alpha-amylase linker (SEQ ID NO: 9)—*A. kawachii* alpha-amylase CBM (SEQ ID NO: 13) in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Commercial Alpha-Amylase Products

Preferred commercial compositions comprising alpha-amylase include MYCOLASE from DSM (Gist Brocades), BAN™, TERMAMYL™ SC, FUNGAMYL™, LIQUOZYME™ X and SAN™ SUPER, SAN™ EXTRA L (Novozymes NS) and CLARASE™ L-40,000, DEX-LO™, SPEYME FRED, SPEZYME™ AA, and SPEZYME™ DELTA AA (Genencor Int.), and the acid fungal alpha-amylase sold under the trade name SP288 (available from Novozymes NS, Denmark).

The acid alpha-amylases may according to the invention be added in an amount of 0.1 to 10 AFAU/g DS, preferably 0.10 to 5 AFAU/g DS, especially 0.3 to 2 AFAU/g DS.

Combination of Glucoamylase and Acid Alpha-Amylase

Even though the presence of acid alpha-amylase is not mandatory according to the invention the activities of acid alpha-amylase and glucoamylase may be present in a ratio of between 0.3 and 5.0 AFAU/AGU. More preferably the ratio between acid alpha-amylase activity and glucoamylase activity is at least 0.35, at least 0.40, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.85, or even at least 1.9 AFAU/AGU. However, the ratio between acid alpha-amylase activity and glucoamylase activity should preferably be less than 4.5, less than 4.0, less than 3.5, less than 3.0, less than 2.5, or even less than 2.25 AFAU/AGU. In AUU/AGI the activities of acid alpha-amylase and glucoamylase are preferably present in a ratio of between 0.4 and 6.5 AUU/AGI. More preferably the ratio between acid alpha-amylase activity and glucoamylase activity is at least 0.45, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4, or even at least 2.5 AUU/AGI. However, the ratio between acid alpha-amylase activity and glucoamylase activity is preferably less than 6.0, less than 5.5, less than 4.5, less than 4.0, less than 3.5, or even less than 3.0 AUU/AGI.

Protease

According to the process of the invention a protease may be present during saccharification and/or fermentation as well.

In a preferred embodiment the protease is an acid protease of microbial origin, preferably of fungal or bacterial origin.

Suitable proteases include microbial proteases, such as fungal and bacterial proteases. Preferred proteases are acidic proteases, i.e., proteases characterized by the ability to hydrolyze proteins under acidic conditions below pH 7.

Contemplated acid fungal proteases include fungal proteases derived from *Aspergillus, Mucor, Rhizopus, Candida, Coriolus, Endothia, Enthomophtra, Irpex, Penicillium, Sclerotium* and *Torulopsis*. Especially contemplated are proteases derived from *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc. Japan* 28: 66), *Aspergillus awamori* (Hayashida et al., 1977, *Agric. Biol. Chem.* 42(5): 927-933, *Aspergillus aculeatus* (WO 95/02044), or *Aspergillus oryzae*, such as the pepA protease; and acidic proteases from *Mucor pusillus* or *Mucor miehei*.

Contemplated are also neutral or alkaline proteases, such as a protease derived from a strain of *Bacillus*. A particular protease contemplated for the invention is derived from *Bacillus amyloliquefaciens* and has the sequence obtainable at Swissprot as Accession No. P06832. Also contemplated are the proteases having at least 90% identity to amino acid sequence obtainable at Swissprot as Accession No. P06832 such as at least 92%, at least 95%, at least 96%, at least 97%, at least 98%, or particularly at least 99% identity.

Further contemplated are the proteases having at least 90% identity to amino acid sequence disclosed as SEQ.ID.NO:1 in the WO 2003/048353 such as at 92%, at least 95%, at least 96%, at least 97%, at least 98%, or particularly at least 99% identity.

Also contemplated are papain-like proteases such as proteases within E.C. 3.4.22.* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

Proteases may be added in the amounts of 0.1-1000 AU/kg dm, preferably 1-100 AU/kg DS and most preferably 5-25 AU/kg DS.

Additional Ingredients

Additional ingredients may be present during saccharification and/or fermentation to increase the effectiveness of the process of the invention. For instance, nutrients (e.g. fermentation organism micronutrients), antibiotics, salts (e.g., zinc or magnesium salts), other enzymes such as phytase, cellulase, hemicellulase, exo and endoglucanase, and xylanases.

Recovery of Fermentation Product

The fermentation product, such as ethanol, may optionally be recovered after fermentation. The recovery may be performed by any conventional manner such as, e.g., distillation.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

Material and Methods

Glucoamylases:

Glucoamylase derived from *Athelia rolfsii* disclosed in SEQ ID NO: 2 and available from Novozymes NS.

Glucoamylase derived from *Aspergillus niger* disclosed in Boel et al. (1984), EMBO J. 3 (5) p. 1097-1102 and available from Novozymes NS.

Glucoamylase derived from *Talaromyces emersonii* disclosed in WO 99/28448 and available from Novozymes NS.

Acid fungal alpha-amylase is derived from *Aspergillus niger* consisting of the *Aspergillus niger* acid alpha-amylase catalytic domain (SEQ ID NO: 3), *Aspergillus kawachii* alpha-amylase linker (SEQ ID NO: 9)—*Aspergillus kawachii* alpha-amylase CBM (SEQ ID NO: 13).

Yeast: Red Star™ Available from Red Star/Lesaffre, USA

Homology/Identity

In context of the present invention "homology" means the degree of identity between two amino acid sequences. The homology may suitably be determined by computer programs known in the art, such as, GAP provided in the GCG program package (Program Manual for the Wisconsin Package, Version 8, August 1994, Genetics Computer Group, 575 Science Drive, Madison, Wis., USA 53711) (Needleman and Wunsch, 1970, *Journal of Molecular Biology* 48: 443-453. The following settings for polypeptide sequence comparison are used: GAP creation penalty of 3.0 and GAP extension penalty of 0.1.

Alpha-Amylase Activity (KNU)

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e. at 37° C.+/−0.05; 0.0003 M Ca²⁺; and pH 5.6) dextrinizes 5260 mg starch dry substance Merck Amylum solubile.

A folder EB-SM-0009.02/01 describing this analytical method in more detail is available upon request to Novozymes NS, Denmark, which folder is hereby incorporated by reference.

Acid Alpha-Amylase Activity

When used according to the present invention the activity of any acid alpha-amylase may be measured in AFAU (Acid Fungal Alpha-amylase Units). Alternatively activity of acid alpha-amylase may be measured in AAU (Acid Alpha-amylase Units).

Acid Alpha-Amylase Units (AAU)

The acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

Standard Conditions/Reaction Conditions:
Substrate: Soluble starch. Concentration approx. 20 g DS/L.
Buffer: Citrate, approx. 0.13 M, pH=4.2
Iodine solution: 40.176 g potassium iodide+0.088 g iodine/L
City water 15-20° dH (German degree hardness)
pH: 4.2
Incubation temperature: 30° C.
Reaction time: 11 minutes
Wavelength: 620 nm
Enzyme concentration: 0.13-0.19 AAU/mL
Enzyme working range: 0.13-0.19 AAU/mL The starch should be Lintner starch, which is a thin-boiling starch used in the laboratory as colorimetric indicator. Lintner starch is obtained by dilute hydrochloric acid treatment of native starch so that it retains the ability to color blue with iodine. Further details can be found in European Patent No. 140410, which disclosure is hereby incorporated by reference.

Acid Alpha-Amylase Activity (AFAU)

Acid alpha-amylase activity may be measured in AFAU (Acid Fungal Alpha-amylase Units), which are determined relative to an enzyme standard. 1 FAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

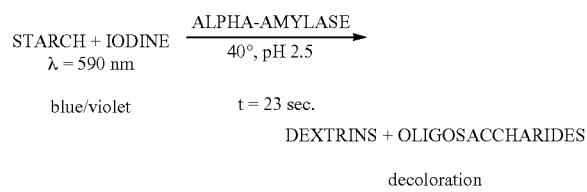

Standard Conditions/Reaction Conditions:

| | |
|---|---|
| Substrate: | Soluble starch, approx. 0.17 g/L |
| Buffer: | Citrate, approx. 0.03M |
| Iodine (I2): | 0.03 g/L |
| CaCl₂: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes NS, Denmark, which folder is hereby incorporated by reference.

Glucoamylase Activity

Glucoamylase activity may be measured in AGI units or in AmyloGlucosidase Units (AGU).

Glucoamylase Activity (AGI)

Glucoamylase (equivalent to amyloglucosidase) converts starch into glucose. The amount of glucose is determined here by the glucose oxidase method for the activity determination. The method described in the section 76-11 Starch—Glucoamylase Method with Subsequent Measurement of Glucose with Glucose Oxidase in "Approved methods of the American Association of Cereal Chemists". Vol. 1-2 AACC, from American Association of Cereal Chemists, (2000); ISBN: 1-891127-12-8.

One glucoamylase unit (AGI) is the quantity of enzyme which will form 1 micromol of glucose per minute under the standard conditions of the method.

Standard Conditions/Reaction Conditions:

| | |
|---|---|
| Substrate: | Soluble starch, concentration approx. 16 g dry matter/L. |
| Buffer: | Acetate, approx. 0.04M, pH = 4.3 |
| pH: | 4.3 |
| Incubation temperature: | 60° C. |
| Reaction time: | 15 minutes |
| Termination of the reaction: | NaOH to a concentration of approximately 0.2 g/L (pH~9) |
| Enzyme concentration: | 0.15-0.55 AAU/mL. |

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

AMG Incubation:

| | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

Color Reaction:

| | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes NS, Denmark, which folder is hereby incorporated by reference.

Proteolytic Activity (AU)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU) is defined as the amount of enzyme which under standard conditions (i.e. 25° C., pH 7.5 and 10 min. reaction time) digests hemoglobin at an initial rate such that there is liberated per minute an amount of TCA soluble product which gives the same color with phenol reagent as one milliequivalent of tyrosine.

A folder AF 4/5 describing the analytical method in more detail is available upon request to Novozymes NS, Denmark, which folder is hereby incorporated by reference.

Example 1

Evaluation of *Athelia rolfsii* Glucoamylase in 'One-Step' Fuel Ethanol Fermentations The relative performance of *Athelia rolfsii* glucoamylase to *Aspergillus niger* glucoamylase and *Talaromyces emersonii* glucoamylase was evaluated via mini-scale fermentations. About 380 g of milled corn (ground in a pilot scale hammer mill through a 1.65 mm screen) was added to about 620 g tap water. This mixture was supplemented with 3 mL 1 g/L penicillin. The pH of this slurry was adjusted to 5.0 with 40% $H_2SO_4$. The dry solid (DS) level was determined in triplicate to be about 32%. Approximately 5 g of this slurry was added to 15 mL tubes.

A two dose dose-response was conducted with each enzyme. Dosages used were 0.3 and 0.6 nmol/g DS. Six replicates of each treatment were run.

After dosing the tubes were inoculated with 0.04 mL/g mash of yeast propagate (Red Star™ yeast) that had been grown for 22.5 hours on corn mash. Tubes were capped with a screw on top which had been punctured with a small needle to allow gas release and vortexed briefly before weighing and incubation at 32° C. 70 hours fermentations were carried out and ethanol yields were determined by weighing the tubes. Tubes were vortexed briefly before weighing. The result of the experiment is shown in Table 1.

It can be seen from Table 1 the ethanol yield per gram DS is significantly higher when using the *Athelia rolfsii* glucoamylase compared to yields for the wild-type *Aspergillus niger* and *Talaromyces emersonii* glucoamylases.

TABLE 1

| Glucoamylase | nmol/g DS | Ethanol yields |
|---|---|---|
| *Athelia rolfsii* | 0.3 | 96.4 |
| *Aspergillus niger* | | 47.2 |
| *Talaromyces emersonii* | | 30.5 |
| *Athelia rolfsii* | 0.6 | 121.9 |
| *Aspergillus niger* | | 87.2 |
| *Talaromyces emersonii* | | 43.4 |

Example 2

Evaluation of *Athelia rolfsii* Glucoamylase in Combination with Acid Fungal Alpha-Amylase in 'One-Step' Saccharification The glucose concentration after one step saccharification with *Athelia rolfsii* glucoamylase alone and in combination with a fungal acid alpha-amylase activity (*Aspergillus niger* acid alpha-amylase hybrid with starch-binding domain from *Aspergillus kawachii* alpha-amylase), respectively, was compared with *Aspergillus niger* glucoamylase alone and in combination the same fungal acid alpha-amylase under the same conditions and at the same dose levels.

The evaluation was made by mini-scale saccharification very similar to the mini-scale fermentation used in Example 1, except for the fact that no yeast was added and a buffer was used to hold the pH at 4.5.

Briefly, 194 g of milled corn was mixed with 306 g of 37 mM NaOAc, 0.025% sodium azide, 20 mM $CaCl_2$, pH 4.5 to yield a slurry of approximately 35% DS. The pH of this slurry was adjusted to 4.5 with 40% $H_2SO_4$ (initial pH, before adjustment, was around 4.9). The slurry was allowed to hydrate while stirring at room temperature for one hour. Approximately 5 g of this slurry was added to a 20 mL vial for each reaction. The vials containing corn slurry were then pre-incubated at 32° C. for one hour prior to dosing. Each vial was dosed with the appropriate amount of enzyme, capped and vortexed immediately. Actual dosages were based on the exact weight of corn slurry in each vial. Three replicates were run for each reaction. Vials were incubated at 32° C. Each vial was vortexed after 4 hours and the reactions were stopped by addition of 50 microL of 40% $H_2SO_4$ and prepped for HPLC analysis. The HPLC preparation consisted of centrifuging, and filtering through a 0.45 micro m filter. Samples awaiting HPLC analysis were stored at 4° C.

TABLE 2 shows the glucose concentration after 4 hours of saccharification.

| Treatment | 4 hour Glucose (g/L) |
|---|---|
| 0.263 mg/g DS *Aspergillus niger* glucoamylase | 33.2 |
| 0.263 mg/g DS *Aspergillus niger* glucoamylase + 0.034 mg/g DS *Aspergillus niger* acid alpha-amylase with *Aspergillus kawachii* alpha-amylase linker and CBM | 40.4 |
| 0.263 mg/g DS *Athelia rolfsii* glucoamylase | 45.6 |
| 0.263 mg/g DS *Athelia rolfsii* glucoamylase + 0.034 mg/g DS *Aspergillus niger* acid alpha- | 63.2 |

TABLE 2-continued shows the glucose concentration after 4 hours of saccharification.

| Treatment | 4 hour Glucose (g/L) |
|---|---|
| amylase with *Aspergillus kawachii* alpha-amylase linker and CBM | |

The obtained glucose level after saccharification correlates with the ethanol fermentation yield that would be obtained if fermented by *Saccharomyces* yeast. Consequently, the above results show that *Athelia rolfsii* glucoamylase alone and in combination with a fungal acid alpha-amylase performs better than *Aspergillus niger* glucoamylase alone and in combination with a fungal acid alpha-amylase under the same conditions.

The invention claimed is:

1. A process for producing a fermentation product, comprising:
   (a) saccharifying a starch-containing material with a glucoamylase at a temperature below the initial gelatinization temperature of the starch-containing material, wherein the glucoamylase comprises the amino acid sequence of amino acids 1-561 of SEQ ID NO: 2, and
   (b) fermenting using a fermenting organism,
wherein the saccharification and fermentation are carried out simultaneously and the temperature during the saccharification and fermentation is between 28° C. and 36° C.

2. The process of claim 1, wherein the sugar concentration is kept at a level below about 3 wt. % during saccharification and fermentation.

3. The process of claim 1, wherein the glucoamylase is present in an amount of 0.1 to 0.5 AGU/g DS.

4. The process of claim 1, wherein the starch-containing material is saccharified in the presence of an alpha-amylase.

5. The process of claim 4, wherein the alpha-amylase is an acid alpha-amylase.

6. The process of claim 5, wherein the acid alpha-amylase is a fungal alpha-amylase.

7. The process of claim 6, wherein the acid alpha-amylase is an *Aspergillus* alpha-amylase.

8. The process of claim 7, wherein the acid alpha-amylase is an alpha-amylase obtained from *A. awamori, A. niger*, or *A. oryzae*.

9. The process of claim 5, wherein the acid alpha-amylase has at least 95% sequence identity to SEQ ID NO: 4.

10. The process of claim 5, wherein the acid alpha-amylase is a hybrid enzyme comprising an alpha-amylase catalytic domain (CD) and a carbohydrate-binding module (CBM) and optionally a linker.

11. The process of claim 10, wherein the CBM is derived from *Aspergillus kawachii* alpha-amylase, *Aspergillus niger* glucoamylase, or *Athelia rolfsii* glucoamylase.

12. The process of claim 10, wherein the hybrid enzyme comprises an *Aspergillus niger* acid alpha-amylase catalytic domain and a CBM from an *Aspergillus kawachii* alpha-amylase.

13. The process of claim 5, wherein the acid alpha-amylase is present in an amount of 0.1 to 10 AFAU/g DS, preferably 0.10 to 5 AFAU/g DS, especially 0.3 to 2 AFAU/g DS.

14. The process of claim 5, wherein the acid alpha-amylase and glucoamylase is added in a ratio of between 0.5 to 3 AFAU/AGU.

15. The process of claim 1, wherein the milled starch-containing material is saccharified with the glucoamylase and two acid alpha-amylases.

16. The process of claim 1, wherein the saccharification and fermentation are carried out at a pH in the range between 3 and 7.

17. The process of claim 1, wherein a slurry comprising water and milled starch-containing material is prepared before step (a).

18. The process of claim 1, wherein the saccharification and fermentation are performed in the presence of an acid protease.

19. The process of claim 1, further comprising recovering the fermentation product after fermentation.

20. The process of claim 1, wherein the fermentation product is ethanol.

\* \* \* \* \*